(12) United States Patent
Gyuricza et al.

(10) Patent No.: US 7,737,177 B2
(45) Date of Patent: Jun. 15, 2010

(54) PROCESSES FOR PREPARING CRYSTALLINE AND AMORPHOUS MUPIROCIN CALCIUM

(75) Inventors: Lorant Gyuricza, Nyekljdhiza (HU); Erszebet Meszaros-Sos, Debrecen (HU); Csaba Szabo, Debrecen (HU); Claude Singer, Kfar Saba (IL)

(73) Assignee: TEVA Gyógyszergyár Zártkörüen Müködö Részvénytárasaság, Debrecen (HU)

( * ) Notice: Subject to any disclaimer, the term of this patent is extended or adjusted under 35 U.S.C. 154(b) by 0 days.

(21) Appl. No.: 10/289,919

(22) Filed: Nov. 6, 2002

(65) Prior Publication Data

US 2004/0024052 A1 Feb. 5, 2004

Related U.S. Application Data

(60) Provisional application No. 60/344,117, filed on Dec. 28, 2001, provisional application No. 60/344,118, filed on Dec. 28, 2001, provisional application No. 60/348,142, filed on Jan. 11, 2002, provisional application No. 60/348,183, filed on Jan. 11, 2002, provisional application No. 60/360,721, filed on Mar. 1, 2002, provisional application No. 60/368,735, filed on Mar. 29, 2002.

(51) Int. Cl.
*A61K 31/335* (2006.01)
(52) U.S. Cl. .................. 514/449; 514/557; 514/724
(58) Field of Classification Search ................ 549/414; 514/451, 460, 475, 529, 557, 738
See application file for complete search history.

(56) References Cited

U.S. PATENT DOCUMENTS

| | | | |
|---|---|---|---|
| 3,954,872 A | 5/1976 | Koppe et al. | |
| 3,977,943 A | 8/1976 | Barrow et al. | |
| 4,071,536 A | 1/1978 | Barrow et al. | |
| 4,222,942 A | 9/1980 | O'Hanlon et al. | |
| 4,289,703 A | 9/1981 | Barrow et al. | |
| 4,524,075 A | 6/1985 | Oduro-Yeboah | |
| 4,639,534 A | 1/1987 | Curzons | |
| 4,786,742 A | 11/1988 | Curzons | |
| 4,790,989 A | 12/1988 | Hunter et al. | |
| 4,879,287 A | 11/1989 | Orr et al. | |
| 4,916,155 A | 4/1990 | Baker et al. | |
| 5,191,093 A | 3/1993 | Baker et al. | |
| 5,405,762 A | 4/1995 | Takahashi et al. | |
| 5,436,266 A | 7/1995 | Baker et al. | |
| 5,569,672 A | 10/1996 | Baker et al. | |
| 5,594,026 A | 1/1997 | Greenway et al. | |
| 6,001,870 A | 12/1999 | Henkel | |
| 6,231,875 B1 | 5/2001 | Sun et al. | |
| 6,245,921 B1 | 6/2001 | Barta et al. | |
| 6,280,593 B1 * | 8/2001 | Wiese et al. | ......... 204/530 |
| 6,489,358 B2 * | 12/2002 | Lavon et al. | ......... 514/460 |
| 6,506,591 B2 | 1/2003 | Szell et al. | |
| 2002/0004063 A1 | 1/2002 | Zhang | |
| 2002/0028227 A1 | 3/2002 | Yu et al. | |
| 2002/0028843 A1 | 3/2002 | Lavon et al. | ......... 514/460 |
| 2002/0035061 A1 | 3/2002 | Krieger et al. | |
| 2004/0039049 A1 | 2/2004 | Weisman et al. | ......... 514/460 |

FOREIGN PATENT DOCUMENTS

| | | |
|---|---|---|
| BE | 870855 | 3/1979 |
| DE | 2227739 | 1/1973 |
| EP | 0 005 614 | 11/1979 |
| EP | 0 251 434 A2 | 1/1988 |
| EP | 1 174 133 A1 | 1/2002 |
| EP | 1 384 721 A1 | 1/2004 |
| GB | 1395907 | 5/1975 |
| GB | 1577730 | 10/1977 |
| GB | 1577545 | 10/1980 |
| JP | 52-70083 | 6/1977 |
| WO | 00/46388 | 8/2000 |
| WO | 00/46389 | 8/2000 |

OTHER PUBLICATIONS

STN online, file DRUGU, Acc. No. 1984-01924 (Schauwecker, Pharm Int. (1983), No. 4, pp. 178-183), Abstract.*
STN online, file DRUGU, Acc. No. 1987-14971 (Brandstaetter et al., Sci. Pharma. (1986), vol. 54, No. 1, pp. 1-10), Abstract.*
European Pharmacopoeia, 4$^{th}$ Ed. pp. 1602-1604, Strasbourg, (2001).

(Continued)

*Primary Examiner*—Johann R Richter
*Assistant Examiner*—Frank I Choi
(74) *Attorney, Agent, or Firm*—Kenyon & Kenyon LLP

(57) ABSTRACT

Processes are provided for preparing mupirocin calcium dihydrate from pseudomonic acid in a two phase system by using an organic carboxylate. A highly pure composition of amorphous mupirocin calcium is provided, and processes for its preparation by solvent removal, lyophilization and precipitation with use of an anti-solvent. Pharmaceutical compositions of amorphous form, and methods of using them to treat infections are also provided. Also provided are combined processes for preparing mupirocin calcium dihydrate and amorphous, by producing amorphous form first, followed by conversion of amorphous form into the dihydrate through crystallization from an aqueous solution. Also provided are processes for removing the water of crystallization of the dihydrate to obtain mupirocin calcium anhydrate.

4 Claims, 11 Drawing Sheets

OTHER PUBLICATIONS

Clayton et al. "The Structure and Configuartion of Pseudomonic Acid C" Tetrahedron Letters 1980, vol. 21, pp. 881-884.

O'Hanlon et al. "The Chemistry of Pseudomonic Acid. Part 6. Structure and Preparation of Pseudomonic Acid D" Journal Chemical Society, Perkin Trans. I 1983, pp. 2655-2657.

Feline et al. "Pseudomonic acid. Part 2. Biosynthesis of Pseudomonic Acid A." Journal Chemical Society, Perkin Trans. I. 1977, pp. 309-318.

Mantle et al. "Radiolabelling of the monate moiety in the study of pseudomonic acid biosynthesis." FEMS Microbiol. Lett. 1989, vol. 59, No. 12, pp. 55-58.

Martin et al. "Biosynthetic studies on pseudomonic acid (mupirocin), a novel antibiotic metabolite of *Pseudomonas fluorescens*." Journal Chemical Society, Perkin Trans. I. 1989, pp. 207-209.

Ward et al. "Mupirocin-A review of Its Antibacterial Activity, Pharmacokinetic Properties and Therapeutic Use," Drugs. 1986, vol. 32, No. 5, pp. 425-444.

Hughes et al. "Interaction of pseudomonic acid A with *Escherichia coli* B isoleucyl-tRNA synthetase." Biochemical Journal. 1980, vol. 191, pp. 209-219.

Chain et al. "Pseudomonic Acid. Part 3. Structure of Pseudomonic Acid B" Journal Chemical Society, Perkin Trans. I. 1977, p. 318-322.

Chain et al. "Structure of Pseudomonic Acid, an Antibiotic from *Pseudomonas fluorescens*." Journal of the Chemical Society, Chemical Communications. Jan. 1974, No. 1, pp. 847-848.

Alexander et al. "The Chemistry of Pseudomonic Acid. Part 1. The Absolute Configuration of Pseudomonic Acid A." Journal of the Chemical Society, Perkin Transactions I, Organic and Bio-organic Chemistry. 1978, pp. 561-565.

Palleroni. "Psuedomonaceae." Bergey's Manual of Systematic Bacteriology. 1984, vol. 1, pp. 141-219.

Harry G. Brittain (Ed.) (1999) "Polymorphism in Pharmaceutical Solids" Drugs and the Pharmaceutical Sciences vol. 95, pp. 183-226 Marcel Dekker, Inc. New York, New York.

Ben Zion Dolitzky et al. Process for Preparing Nateglinide and Intermediates Thereof U.S. Appl. No. 60/413,622, filed Sep. 25, 2002.

Harry G. Brittain (Ed.) (1999) "Polymorphism in Pharmaceutical Solids" Drugs and the Pharmaceutical Sciences vol. 95, pp. 395-419 Marcel Dekker, Inc. New York, New York.

Fuller et al. "Pseudomonic Acid: an Antibiotic produced by *Pseudomonas fluorescens*" Nature, vol. 234, p. 416-417, (1971).

\* cited by examiner

PXRD PATTERN FOR EXAMPLE 6 (MUPIROCIN CALCIUM DIHYDRATE)

PXRD PATTERN FOR EXAMPLE 15 (MUPIROCIN CALCIUM DIHYDRATE)

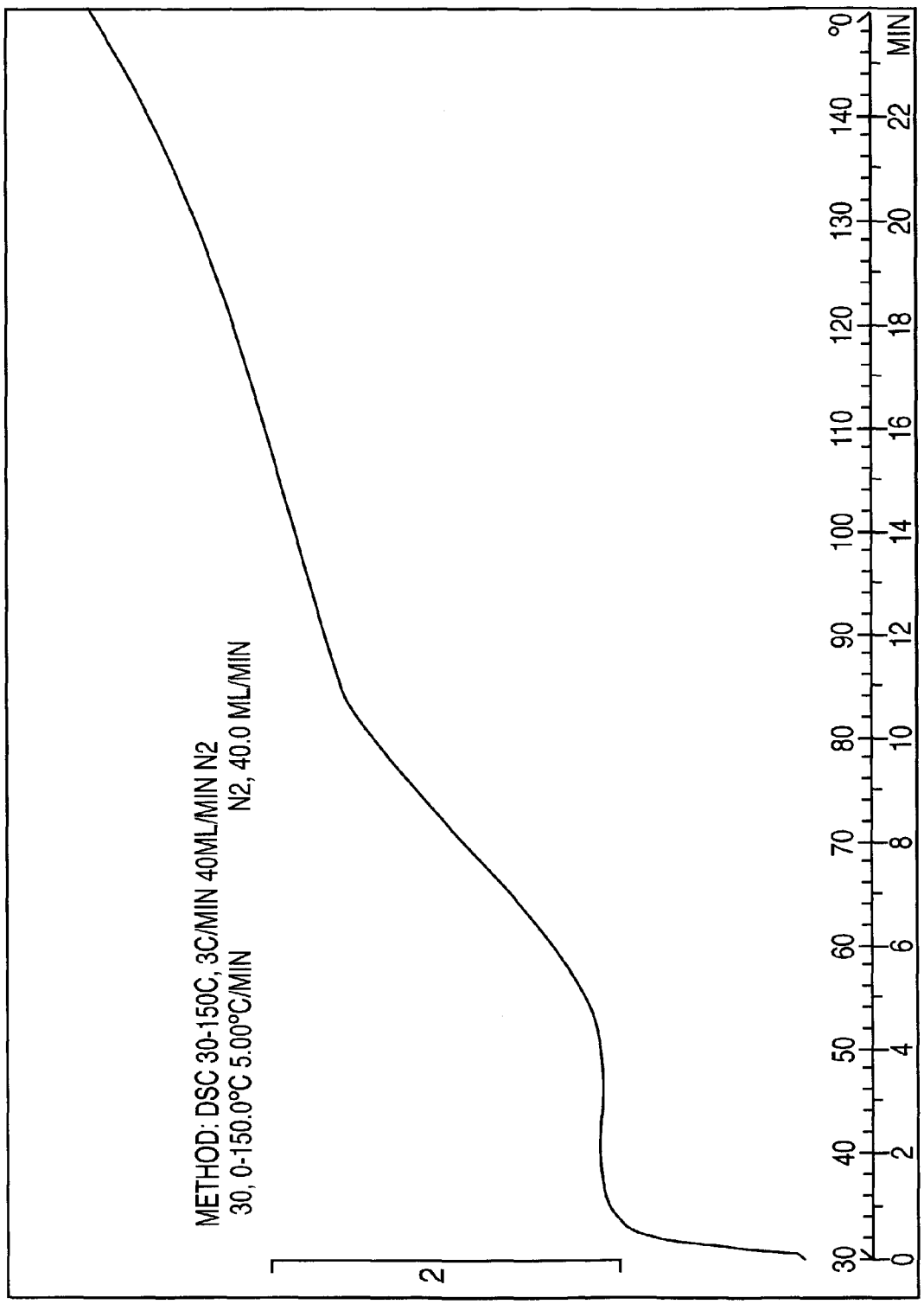
FIG. 7 DSC (AMORPHOUS CALCIUM MUPIROCIN)

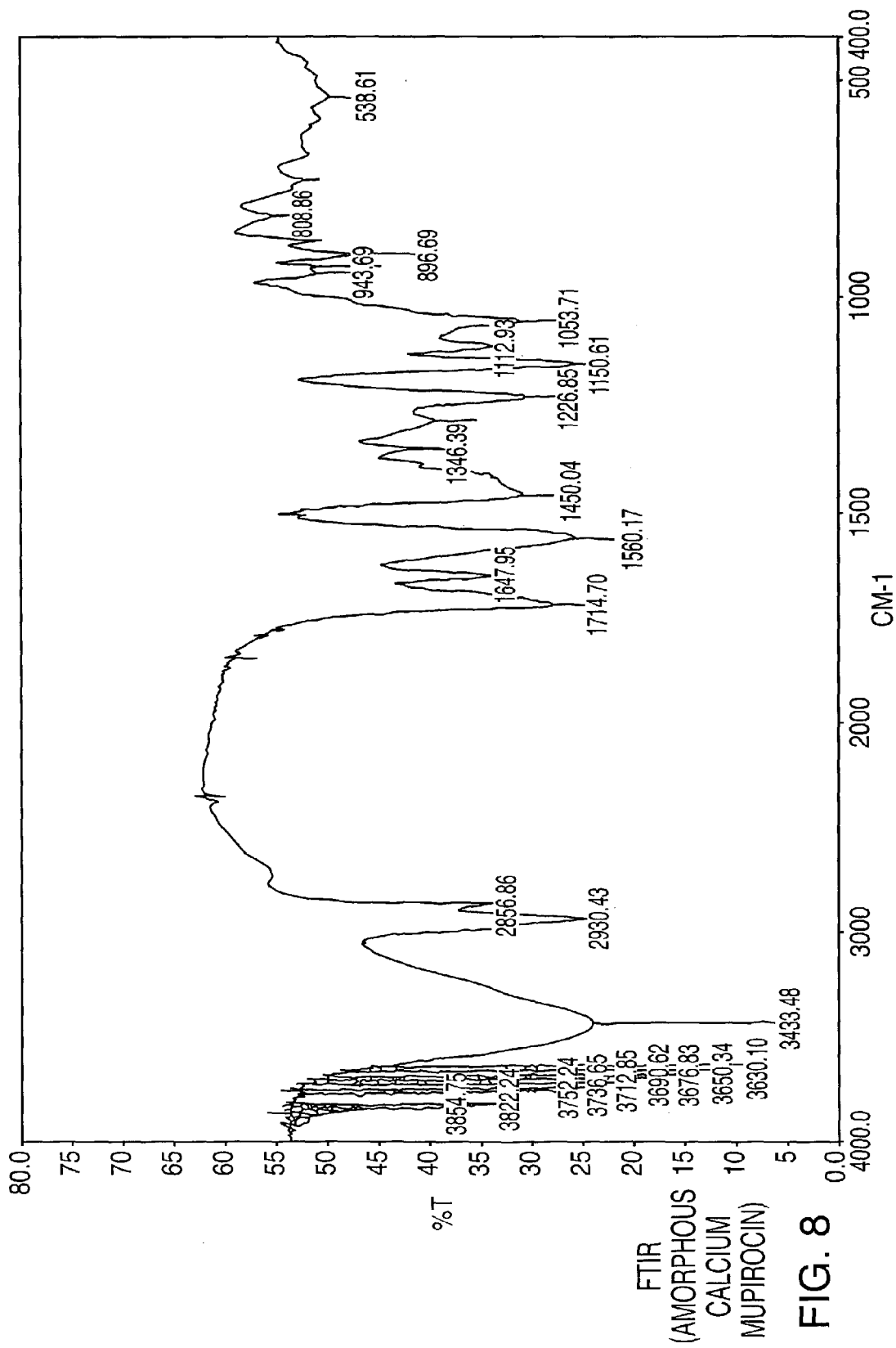
FIG. 8 FTIR (AMORPHOUS CALCIUM MUPIROCIN)

PRODUCT NAME: MUPIROCIN-CALCIUM AMORPHOUS BY PROCESS OF US PATENT:5,436,266 EX 7

PACKING SYSTEM: GLASS
STABILITY PROGRAM TYPE: 25 °C, RH 60%

| PERIOD (WEEK) | ASSAY % (HPLC) | WATER % | IMPURITIES AND DEGRADATION PRODUCTS (HPLC) | | | | | | | |
|---|---|---|---|---|---|---|---|---|---|---|
| | | | MUP E | MUP I | MUP II | MUP D | MUP B | MUP C | RRT 2.3 | TOTAL |
| | 94-100.5 (PROCESS OF PRESENT INVENTION) | <1.5 | <1.0 | <1.0 | <1.0 | <2.5 | <1.0 | <1.0 | <1.0 | <4.5 |
| 0 | | | 0.18 | 0.24 | 0.45 | 1.47 | 0.10 | 0.19 | 0.13 | 2.76 |
| 1 | | | 0.18 | 0.17 | 0.47 | 1.45 | 0.10 | 0.20 | 0.15 | 2.72 |
| 2 | | 0.79 | 0.17 | 0.18 | 0.54 | 1.40 | 0.10 | 0.18 | 0.15 | 2.72 |
| 3 | | | 0.18 | 0.19 | 0.60 | 1.44 | 0.10 | 0.15 | 0.10 | 2.76 |
| 4 | | | 0.19 | 0.24 | 0.71 | 1.56 | 0.12 | 0.20 | 0.14 | 3.16 |
| 6 | | | 0.19 | 0.32 | 0.87 | 1.49 | 0.11 | 0.19 | 0.14 | 3.31 |
| 8 | | | 0.19 | 0.39 | 1.04 | 1.55 | 0.12 | 0.20 | 0.15 | 3.64 |
| 12 | | | 0.22 | 0.50 | 1.44 | 1.71 | 0.14 | 0.23 | 0.17 | 4.41 |

QL = 0.1 W/W% ACCORDING TO EP
THE ASSAY DISCLOSED IS THAT OF AMORPHOUS MUPIROCIN CALCIUM STABILITY REPORT
PREPARED BY THE PROCESS OF THE PRESENT INVENTION. THE ASSAY IS BEING USED
FOR COMPARISON PURPOSES.

FIG. 9

PRODUCT NAME: MUPIROCIN-CALCIUM AMORPHOUS BY PROCESS OF US PATENT:5,436,266 EX 7

PACKING SYSTEM: GLASS
STABILITY PROGRAM TYPE: 2-8 °C, RH 60%

| PERIOD (WEEK) | ASSAY % (HPLC) | WATER % | IMPURITIES AND DEGRADATION PRODUCTS (HPLC) | | | | | | | | |
|---|---|---|---|---|---|---|---|---|---|---|---|
| | | | MUP E | MUP I | MUP II | MUP D | MUP B | MUP C | RRT 2.3 | TOTAL |
| | 94-100.5 (PROCESS OF PRESENT INVENTION) | <1.5 | <1.0 | <1.0 | <1.0 | <2.5 | <1.0 | <1.0 | <1.0 | <4.5 |
| 0 | | | 0.18 | 0.24 | 0.45 | 1.47 | 0.10 | 0.19 | 0.13 | 2.76 |
| 1 | | | 0.18 | 0.16 | 0.39 | 1.45 | 0.10 | 0.20 | 0.15 | 2.63 |
| 2 | | 0.85 | 0.17 | 0.15 | 0.40 | 1.40 | 0.10 | 0.18 | 0.14 | 2.54 |
| 3 | | | 0.18 | 0.14 | 0.38 | 1.43 | <QL | 0.15 | 0.10 | 2.38 |
| 4 | | | 0.19 | 0.18 | 0.41 | 1.55 | 0.12 | 0.20 | 0.14 | 2.79 |
| 6 | | | 0.19 | 0.24 | 0.47 | 1.49 | 0.11 | 0.19 | 0.14 | 2.83 |
| 8 | | | 0.19 | 0.28 | 0.50 | 1.55 | 0.12 | 0.21 | 0.15 | 3.00 |
| 12 | | | 0.22 | 0.32 | 0.57 | 1.73 | 0.14 | 0.23 | 0.17 | 3.38 |

QL = 0.1 W/W% ACCORDING TO EP
THE ASSAY DISCLOSED IS THAT OF AMORPHOUS MUPIROCIN CALCIUM
PREPARED BY THE PROCESS OF THE PRESENT INVENTION. THE ASSAY IS BEING USED
FOR COMPARISON PURPOSES.

STABILITY REPORT    FIG. 10

MUPIROCIN IMPURITIES

PROCESSES FOR PREPARING CRYSTALLINE AND AMORPHOUS MUPIROCIN CALCIUM

CROSS-REFERENCE TO RELATED APPLICATIONS

This application claims the benefit of the following U.S. Provisional Applications: No. 60/344,117, filed Dec. 28, 2001; Ser. No. 60/344,118, filed Dec. 28, 2001; Ser. No. 60/348,142, filed Jan. 11, 2002; Ser. No. 60/348,183, filed Jan. 11, 2002; Ser. No. 60/360,721, filed Mar. 1, 2002; and No. 60/368,735, filed Mar. 29, 2002.

FIELD OF THE INVENTION

The present invention relates to the solid state chemistry of the antibiotic pseudomonic acid A. Particularly, the present invention relates to processes for preparing crystalline and amorphous forms of mupirocin calcium.

BACKGROUND OF THE INVENTION

Pseudomonic acid A is an antibiotic that has a growth inhibiting effect mainly against Gram positive bacteria (e.g. *Staphylococcus aureus, Streptococcus pyogenes, Streptococcus pneumoniae, Klebsiella pneumoniae*) and some Gram negative bacteria (e.g. *Haemophilus influenzae, Neisseria gonorrhoeae*) [A. Ward, D. M. Campoli-Richards, Drugs 32, 425-444 (1986)] and its minimal inhibiting concentration is in the range of 0.02-0.5 $mg/dm^3$. Pseudomonic acid A, by inhibiting the isoleucine-tRNA synthase enzyme, affects the peptide synthesis of pathogen bacteria [J. Hughes and G. Mellows, Biochem. J. 191, 209-219 (1980)]. An advantageous feature of this antibiotic is that it has very low toxicity both for humans and animals and it is negative in the Ames test. Pseudomonic acid A is presently used in human therapy, in various formulations, for the treatment of skin infections (e.g. impetigo, pyoderma), nose and external ear infections, acne, burns, eczema, psoriasis, in case of ulceration for treatment of secondary infections, and for prevention of hospital infections.

The chemical structure of pseudomonic acid A is 9-{4[5S (2S,3S-epoxy-5S-hydroxy-4S-methylhexyl)-3R,4R-dihydroxy-tetrahydropyran-2S-yl]-3-methylbut-2(E)-enoyloxy}nonanoic acid [E. B. Chain and G. Mellows, J. C. S. Chem. Comm. 847-848 (1974); R. G. Alexander, J. P. Clayton, K. Luk, N. H. Rogers, T. J. King, J. C. S. Perkin I. 561-565 (1978)], as depicted by formula (I):

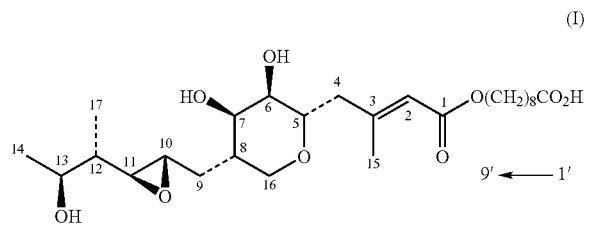

It is known that *Pseudomonas fluorescens* is able to produce the pseudomonic acid A. According to the British Patent No. 1,395,907, the *Pseudomonas fluorescens* NCIB 10586 strain is able to biosynthesize the pseudomonic acid complex consisting of pseudomonic acid A and its isomer being a double bond in the cis position between the carbon atoms $C_2$ and $C_3$ and pseudomonic acid B. The ratio of the components is 4.5:4.5:1. According to the Japanese patent application No. 52-70083, however, the *Pseudomonas fluorescens* Y-11633 strain is able to biosynthesize the pseudomonic acid complex consisting of the pseudomonic acid A, pseudomonic acid B and further two components with unknown structures in the ratio of 9:0.5:0.5.

Mupirocin calcium, an antibiotic derived from pseudomonic acid is currently marketed in the United States as Bactroban®. Bactroban® is recommended for treatment of secondarily infected traumatic skin lesions caused by strains of *Staphylococcus aureus* and *Streptococcus pyogenes*. Bactroban® is sold as a topical cream or a nasal ointment and has a calcium salt strength of 2% equivalent base. According to the maker of Bactroban®, mupirocin calcium could be administered orally at 500 mg, and intravenously at 250 mg without any major side effects.

Mupirocin calcium is especially effective against gram-positive bacteria, but may also be used against gram negative bacteria. It inhibits bacterial protein synthesis by irreversibly binding to bacterial isoleucyl transfer-RNA synthetase.

The calcium salt of pseudomonic acid ("mupirocin calcium") has been disclosed in various patents. U.K. Pat. Nos. 1,577,545 and 1,577,730, incorporated herein by reference, disclose the use of mupirocin calcium in the treatment of diseases. The '545 patent is directed to the treatment and prevention of swine dysentery with the calcium salt of mupirocin. The '730 patent is directed to the use of the calcium salt of mupirocin to treat respiratory, venereal and mycoplasma-induced diseases in non-human mammals. The disclosure focuses on the efficacy of mupirocin as a drug, rather than its preparation.

U.S. Pat. No. 4,879,287 is directed to a pharmaceutical composition of mupirocin calcium for topical administration comprising hydrated crystalline calcium salt, and a corticosteroid. The '287 patent discloses various formulations for crystalline mupirocin calcium and is incorporated herein by reference.

U.S. Pat. Nos. 5,596,672, 5,436,266, 5,191,093 and 4,916,155 (Baker et al.), all within the same family, disclose a crystalline calcium salt of mupirocin, and claim its composition, method of preparation and administration. All these patents are incorporated herein by reference. The '672 patent is directed to a method of treating bacterial infections with crystalline mupirocin calcium or a hydrate thereof. The '266 patent is directed to a hydrate of crystalline mupirocin calcium. The '155 patent is directed to anhydrous crystalline mupirocin calcium. The '093 patent is directed to a process for preparing crystalline mupirocin calcium or a hydrate thereof by "reacting pseudomonate ions with calcium ions in solution in an aqueous solvent, recovering a crystalline calcium pseudomonate hydrate from the solution and thereafter optionally removing water of crystallization."

The Baker et al. patents disclose preparing amorphous form of mupirocin calcium by crystallization from an aqueous solution consisting of 50% methanol followed by trituration with dry ether. Amorphous mupirocin calcium obtained in the patents exhibits a relatively low melting point of 70-76° C., a relatively low assay of 89.9% (expressed as a percentage of pure free pseudomonic acid) and rapid deterioration at high temperatures (chart in Columns 8 and 9 of the '093 and related patents). The Baker et al. patents disclose that "the readily isolable amorphous form of this salt has been found to be sparingly water soluble material, having a low melting point and poor thermal stability." (Column 1, Lines 31-33).

U.S. Pat. No. 4,639,534, incorporated herein by reference, discloses use of a lithium salt as an intermediate in isolating pseudomonic acid from a broth. The '534 patent extracts the broth to obtain mupirocin lithium and hydrolyzes the salt to obtain pseudomonic acid.

A need exists in the art to prepare mupirocin calcium dihydrate with new processes. Processes which eliminate the use of a co-solvent are particularly preferred in that removal of a co-solvent is a tedious step and may lead to deterioration of the product. A need also exists in the art for a process for preparing a more pure and stable form of amorphous mupirocin calcium.

SUMMARY OF THE INVENTION

In one aspect, the present invention provides a process for preparing crystalline mupirocin calcium hydrate or an anhydrate thereof comprising the steps of preparing a solution of pseudomonic acid in a water-immiscible solvent, combining the solution with a solution or a suspension of a calcium $C_2$ to $C_{12}$ organic carboxylate in an aqueous solvent, to form an aqueous and a non-aqueous phase, wherein mupirocin calcium dihydrate precipitates from the aqueous phase, separating the precipitate and optionally converting the dihydrate to the anhydrate. Preferably, the aqueous suspension or solution is water free of a co-solvent or a mixture of water and a $C_1$ to a $C_4$ alcohol. Preferred organic carboxylates are acetate, propanoate and hexanoate, with alkyl substituted hexanoates such as 2-ethyl-hexanoate being more preferred.

In another aspect, the present invention provides a process for preparing crystalline mupirocin calcium hydrate or an anhydrate thereof comprising the steps of adding pseudomonic acid and a calcium $C_2$ to $C_{12}$ organic carboxylate to an aqueous solvent to form a solution, wherein a $C_2$ to $C_{12}$ organic carboxylic acid forms, removing the carboxylic acid, separating mupirocin calcium dihydrate as a precipitate from the aqueous solvent and optionally converting the dihydrate to the anhydrate. Preferably, the solvent is a mixture of water and a $C_1$ to a $C_4$ alcohol whose water content is increased before the crystallization step. Preferably, the carboxylic acid is removed by extraction.

In another aspect, the present invention provides a process for preparing crystalline mupirocin calcium dihydrate or an anhydrate thereof comprising the steps of adding pseudomonic acid and calcium oxide to water free of a co-solvent to form a solution, wherein mupirocin calcium dihydrate precipitates from the solution, separating the mupirocin calcium dihydrate and optionally converting the dihydrate to the anhydrate.

In another aspect, the present invention provides a process for preparing amorphous mupirocin calcium comprising the steps of adding pseudomonic acid, a base and a source of calcium ions to a $C_1$ to a $C_4$ alcohol to form a solution and removing the alcohol. Preferably, the alcohol is substantially anhydrous, more preferably has less than about 1% (vol/vol) water content and is selected from the group consisting of methanol and ethanol. Preferably, the alcohol is removed by evaporation.

In another aspect, the present invention provides a process for preparing amorphous mupirocin calcium comprising the steps of adding pseudomonic acid, a base and a source of calcium ions to a $C_1$ to a $C_4$ alcohol to form a solution, combining the solution with an anti-solvent to precipitate amorphous mupirocin calcium and separating the precipitate. Preferably, the alcohol has less than about 1% (vol/vol) water content and is ethanol or methanol. The anti-solvent is preferably an ester and an ether, such as methyl-t-butyl ether, diisopropylether and i-butyl-acetate. Preferably, the solution is added to the anti-solvent.

In another aspect, the present invention provides a process for preparing amorphous mupirocin calcium comprising the steps of adding pseudomonic acid, a base and a source of calcium ions to a solvent selected from the group consisting of water, a $C_1$ to a $C_4$ alcohol and mixtures thereof to form a solution and lyophilizing the solution. Preferably the alcohol is methanol.

In another aspect, the present invention provides a process for preparing crystalline mupirocin calcium dihydrate or an anhydrate thereof comprising the steps of dissolving pseudomonic acid in a water-immiscible solvent to form a solution, combining the solution with a solution or suspension of a base and a source of calcium ions in an aqueous solvent, to form an aqueous and a non-aqueous phase, wherein mupirocin calcium dihydrate precipitates from the aqueous phase, separating the dihydrate and optionally converting the dihydrate to the anhydrate. Preferably the water-immiscible solvent is selected from the group consisting of esters and ketones, such as isobutyl acetate and isobutyl methyl ketone.

In another aspect, the present invention provides a process for preparing amorphous mupirocin calcium comprising the steps of reacting pseudomonate ions and calcium ions in solution in a $C_1$ to a $C_4$ alcohol and evaporating the alcohol.

In another aspect, the present invention provides a process for preparing amorphous mupirocin calcium comprising the steps of reacting pseudomonate ions and calcium ions in solution in a $C_1$ to a $C_4$ alcohol, adding the solution to an ester or an ether as an anti-solvent to precipitate amorphous mupirocin calcium and separating the precipitate.

In another aspect, the present invention provides a process for preparing amorphous mupirocin calcium comprising the steps of reacting pseudomonate ions and calcium ions in solution in water or a mixture of water and a $C_1$ to a $C_4$ alcohol and lyophilizing the solution.

In another aspect, the present invention provides a process for preparing crystalline mupirocin calcium dihydrate or an anhydrate thereof comprising the steps of providing pseudomonic acid and a calcium $C_2$ to $C_8$ organic carboxylate, exchanging acidic proton of the pseudomonic acid with the calcium ion of the $C_2$ to $C_8$ organic carboxylate, recovering the mupirocin calcium dihydrate and optionally converting the dihydrate to the anhydrate.

The processes for preparing amorphous and dihydrate mupirocin calcium can be combined, by first preparing amorphous form and then obtaining the dihydrate from amorphous form. The dihydrate can optionally be desolvated, if desired, to obtain the anhydrate form.

The present invention provides pharmaceutical compositions of amorphous mupirocin calcium and methods of their use in preventing or treating infections.

BRIEF DESCRIPTION OF THE DRAWINGS

FIG. 7 is a Differential Scanning Calorimetry ("DSC") thermogram of amorphous mupirocin calcium.

FIG. 8 is a Fourier Transform Infrared ("FTIR") spectrum of amorphous mupirocin calcium.

FIG. 9 is the thermal stability data of amorphous mupirocin calcium prepared by the process of the prior art.

FIG. 10 is the thermal stability data of amorphous mupirocin calcium prepared by the process of the prior art.

DETAILED DESCRIPTION OF THE INVENTION

The term "pseudomonate" refers to the ion obtained by removing a hydrogen from the carboxylic acid group of pseudomonic acid. Pseudomonate calcium is synonymous with mupirocin calcium.

As used herein, the term "co-solvent" refers to a second solvent used in combination with a first solvent in such amounts to provide desirable solubility properties. Impurities and traces of a solvent are not co-solvents. Hence, water free of co-solvent can include small amounts of other solvents.

As used herein, the term "assay" refers to a determination of purity/presence of a quantity of a substance as described by the European Pharmacopoeia ("EP"). EUROPEAN PHARMACOPOEIA, Fourth Edition, pp 1602-1604, Council of Europe, Strasbourg, 2001. The assay is done with high pressure liquid chromatography ("HPLC").

Baker et al. expresses its assay in relation to psuedomonic acid. The assay of the present invention is expressed differently, as illustrated by Table-1.

TABLE 1

Conversion of the assay disclosed in Baker et al.

| Sample | Crystalline mupirocin calcium dihydrate | | Anhydrous amorphous mupirocin calcium | Pseudomonic acid |
|---|---|---|---|---|
| Melting Point (° C.) | 125–137 | | 70–76 | 73–75 |
| Purity (%) | 92.1* | 98.88** | 89.9* 93.29*** | 91.9* |
| Purity after storage | | | | |
| 10 days, 50° C. | 91.08 | 97.79 | 74.88 77.70 | 71.59 |
| 8 days, 80° C. | 89.33 | 95.91 | 26.07 27.05 | 0 |
| 2 weeks, 37° C. | 92.28 | 99.08 | 87.83 91.14 | 90.61 |
| 2 weeks, 50° C. | 90.90 | 97.60 | 72.0 74.71 | 51.18 |
| 2 weeks, 80° C. | 86.57 | 92.95 | 12.58 13.05 | 0 |

*expressed as a percentage of pure free pseudomonic acid.
**expressed as a percentage of mupirocin calcium dihydrate.
***expressed as a percentage of mupirocin calcium anhydrous.

In connection with amorphous mupirocin calcium, the assay of the present invention can be converted into the assay expressed as in Baker et al. by multiplying with a factor of 0.9637. This 89.9% assay of Baker et al. corresponds to a 93.29% assay as calculated by the method of the present invention.

In connection with mupirocin calcium dihydrate, the 92.1% assay of Baker et al. corresponds to a 98.88% assay as expressed by the present invention.

As used herein, the term "total impurity" refers to the sum of all areas under the peaks of impurities as described by the European Pharmacopoeia. It is determined by another HPLC method and is different than the assay.

The following hypothetic further explains the relationship between the assay and the impurities. For example, lets assume one is provided an active pharmaceutical ingredient with 99% chemical purity (+1% impurity). After final drying, 3% water content (KF) is measured. Assay analysis should give 96%. This is "assay as is". Then one calculates with the water inside to get assay to dry (or simply "assay"), which should give 99%.

Figure 6:
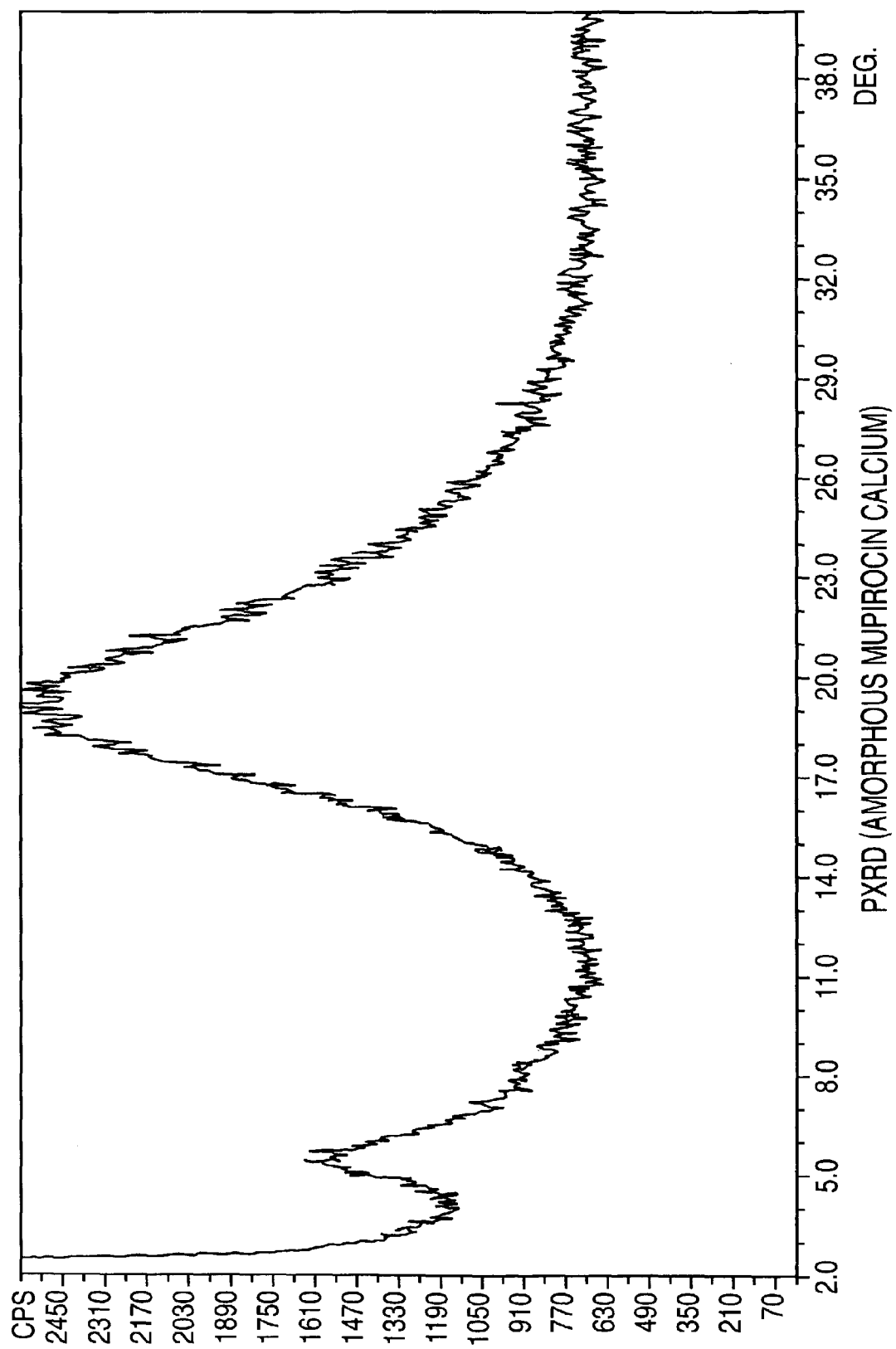
FIG. 6 is a PXRD pattern of amorphous mupirocin calcium.

The present invention provides for a highly purified amorphous form of mupirocin calcium. The amorphous character and purity of the material we have produced is confirmed by a powder X-ray diffraction pattern obtained from a sample thereof, which is provided as FIG. 6. The pattern is without intense focused reflections.

Amorphous mupirocin calcium prepared by the present invention is also characterized by a DSC thermogram depicted in FIG. 7. The DSC thermogram does not show any discernible endotherms or exotherms. The FTIR spectrum (FIG. 8) exhibits the same peaks as those of amorphous mupirocin in the prior art.

The present invention provides amorphous mupirocin calcium with a melting point of about 76° C. to about 89° C., more preferably of about 85° C. to about 89° C. The high melting point of amorphous mupirocin calcium confirms the high purity of the product.

The present invention provides for amorphous mupirocin calcium with high thermal stability. Thermal stability is defined as the ability to resist chemical degradation during storage, especially in light of the conditions during storage. The higher purity and melting points of amorphous mupirocin calcium makes it less susceptible to chemical degradation during storage.

As demonstrated in Table 2, after 2 months of storage at about 25° C. and at about 2-8° C., the amorphous mupirocin calcium has an assay of about 96% as determined by the method of the present invention. Additionally, the total impurity content is almost unchanged at about 3% after 2 months.

TABLE 2a

Thermal stability of 1 Kg batch of amorphous mupirocin calcium prepared by the process of Example 17.

| Period (months at 25° C.) | Assay | Water | Total Impurity |
|---|---|---|---|
| 0 | 98.5 | 1.5 | Error |
| 0.5 | 97.4 | 1.2 | 2.83 |
| 1 | 98.3 | 1.9 | 3.18 |
| 2 | 96.5 | 1.5 | 3.21 |

TABLE 2b

Thermal stability of 1 Kg batch of amorphous mupirocin calcium prepared by the process of Example 17.

| Period (months at 2–8° C.) | Assay | Water | Total Impurity |
|---|---|---|---|
| 0 | 98.5 | 1.2 | Error |
| 0.5 | 95.2 | 1.3 | 2.71 |
| 1.0 | 95.5 | 1.9 | 2.88 |
| 2.0 | 96.7 | 1.6 | 2.86 |

TABLE 2c

Thermal stability of 187.2 grams batch of amorphous mupirocin calcium prepared by the process of Example 17.

| Storage Cond. | Period (Month) | Description | Assay (HPLC) (%) | Water (%) | Impurities (HPLC) (%) | | |
|---|---|---|---|---|---|---|---|
| | | | | | Imp. C | MUP II | Total Impurities |
| Specifications | | White or almost white powder | 93.0 to 100.5 | NMT 1.5 | NMT 2.5 | NMT 1.0 | NMT 4.5 |
| 2° C.-8° C. 60% RH | 0 | White powder | 96.0 | 0.6 | 1.31 | 0.31 | 2.22 |
| | 1 | White powder | 95.6 | 0.8 | NA | NA | NA |
| | 2 | White powder | 95.3 | 0.7 | 1.32 | 0.41 | 2.43 |
| | 3 | White powder | 96.1 | 1.1 | 1.35 | 0.42 | 2.62 |

TABLE 2d

Thermal stability of 187.2 grams batch of amorphous mupirocin calcium prepared by the process of Example 17.

| Storage Cond. | Period (Month) | Description | Assay (HPLC) (%) | Water (%) | Impurities (HPLC) (%) | | |
|---|---|---|---|---|---|---|---|
| | | | | | Imp. C | MUP II | Total Impurities |
| Specifications | | White or almost white powder | 93.0 to 100.5 | NMT 1.5 | NMT 2.5 | NMT 1.0 | NMT 4.5 |
| 25° C./ 60% RH | 0 | White powder | 96.0 | 0.6 | 1.31 | 0.31 | 2.22 |
| | 1 | White powder | 97.5 | 0.8 | NA | NA | NA |
| | 2 | White powder | 94.1 | 0.8 | 1.34 | 0.77 | 3.02 |
| | 3 | White powder | 95.9 | 1.0 | 1.37 | 0.89 | 3.25 |

The thermal stability of amorphous mupirocin calcium prepared by the process of Baker et al. shows a more rapid deterioration. FIGS. 9 and 10 demonstrate that the total level of impurities of amorphous mupirocin calcium is more than about 3.5% (not assay) after two months of storage with the method of Baker et al., whereas mupirocin calcium amorphous prepared according to the method of the present invention has a total level of impurity level of less than about 3.5% (not assay) and more preferably less than about 3.3% after at least two months of storage at 25° C. The amorphous mupirocin calcium of the present invention is particularly stable in regard to an impurity labeled MUP II (Referred to as impurity E in the European Phamacopoia (EP), where storage at 25° C. and RH 60% for at least two months results in a level of the impurity of NMT about 1%, more preferably less than about 0.8%, whereas amorphous mupirocin calcium produced by the art reaches a level of more than 1% after storage for one month.

Figure 11:
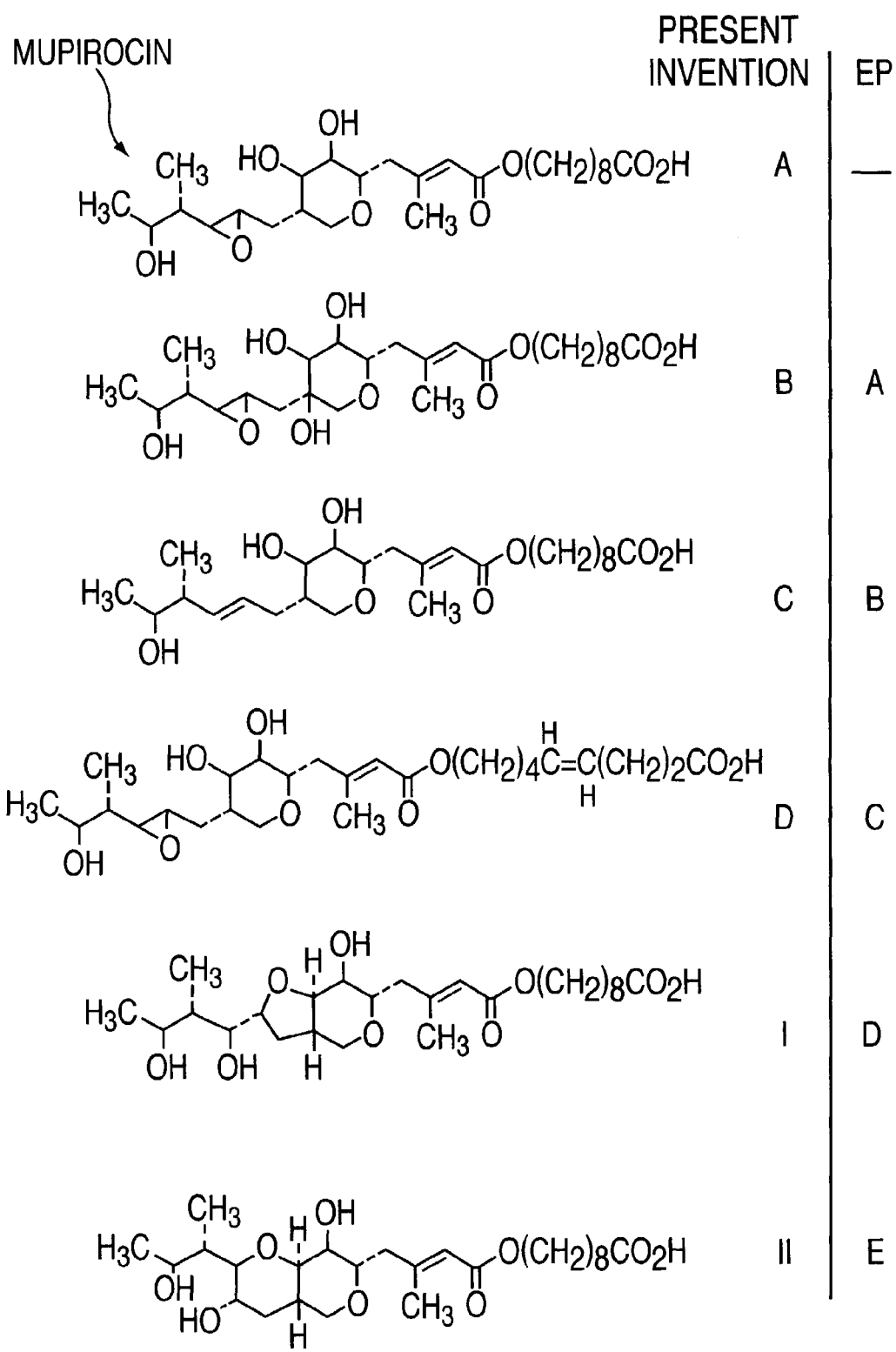
FIG. 11 is an illustration of the various impurities of mupirocin and how they are referred to in the present invention and in the European Pharmacopoeia ("EP").

As illustrated in FIG. 11, the impurities of the present invention correspond to the EP in the following matter: IMP A of EP is B of the present invention; B of EP is C; C of EP is D; D of EP is I (one); E of EP is II (two); and F of EP is E of the present invention.

The present invention provides a process for preparing amorphous mupirocin calcium comprising the steps of adding pseudomonic acid, a base, and a source of calcium ions to a $C_1$ to a $C_4$ alcohol to form a solution, and removing the alcohol. To prepare the solution, pseudomonic acid is dissolved in a $C_1$ to a $C_4$ alcohol, with methanol and ethanol being preferred. Preferably, the alcohol used is substantially anhydrous. The alcohols used preferably contain less than about 2% water, more preferably less than about 1% water (vol/vol).

After preparing a solution of pseudomonic acid in the alcohol, a base is added to the solution, resulting in pseudomonate ions. Bases such as sodium or potassium hydroxide can be used to neutralize the acid. Since neutralization of an acid with a base is well known in the art, one of skill in the art would appreciate that other alternatives can be used.

The amount and concentration of the base used need not be exact. It is the amount which is sufficient to neutralize a substantial part of the pseudomonic acid. One of skill in the art can appreciate that different amounts of base used can be determined in a routine fashion, and variations in the amount of base used may not change the results.

To obtain amorphous mupirocin calcium, a source of calcium ions is added to the solvent. The present invention only requires the addition of calcium ions, and it is not as relevant what ion the calcium can be complexed with as long as the other ion does not interfere with the result. In one embodiment, the present invention uses a calcium salt of a halogen, such as calcium chloride. The base and source of calcium ions can be a single chemical species, e.g., calcium oxide or two different chemical species. The term "a base and source of calcium ions" encompasses use of a single chemical species.

After the addition of all the necessary ingredients, the solution can be stirred. The solution can be stirred from about 30 minutes to about two hours. Stirring often influences the quality and quantity of the crystals, which one of skill in the art can appreciate.

Depending on the base and calcium ions used, a separation step can be used to remove impurities such as salts formed as a result of the presence of excess ions in the solution. In one embodiment potassium hydroxide and calcium chloride are used as a base and a source of calcium ions. After addition of potassium hydroxide and calcium chloride, the unused potassium and chloride ions form a salt that can be separated. Preferably, a filter is used to separate the formed potassium chloride.

The solvent is then removed from the solution. Most preferably the solvent is removed by evaporation. Various techniques well known in the art can be used to evaporate the solvent. For example, the solvent can be evaporated under ambient or reduced pressure, depending upon the volatility of the solvent. In a another embodiment, the solution can be heated to accelerate the evaporation. With high volatile solvents such as methanol, the additional heating step may not be necessary. The solvent can also be evaporated with a rotary evaporator at ambient or reduced pressure.

After removal of the solvent, the residue can be optionally dried to reduce the amount of residual solvent. Drying can be done according to procedures well known in the art. The residue can be dried at ambient or reduced pressure. It can optionally be heated to accelerate the drying process, though it should not be heated beyond the melting point of amorphous mupirocin calcium. Preferably, the product is heated from about 30° C. to about 50° C., most preferably no more than about 45° C. A vacuum oven known in the art can be used.

In another embodiment, amorphous mupirocin calcium is prepared by a process comprising the steps of adding pseudomonic acid, a base and a source of calcium ions to a $C_1$ to a $C_4$ alcohol to form a solution, combining an anti-solvent with the solution to precipitate amorphous mupirocin calcium and separating the precipitate. As used herein, the term "anti-solvent" has its ordinary meaning in the art and refers to a liquid that is added to a solvent to reduce the solubility of a compound, such as a salt, in that solvent, resulting in precipitation of the salt. Mupirocin calcium has low solubility for the anti-solvent, causing the salt to precipitate. The solution can be prepared by combining methanolic solutions of pseudomonic acid, a base such as potassium hydroxide and a source of calcium ions, such as calcium chloride. The resulting solution can then be filtered to remove impurities, as described above. Preferred solvents are $C_1$ to $C_4$ alcohols, particularly methanol. The alcohols used preferably have a water content of less than about 2%, more preferably less than about 1%.

The anti-solvent is then combined with the solution, preferably by adding the solution to the anti-solvent. The anti-solvent is preferably an ether, wherein each radical of the ether is selected from a $C_1$ to a $C_4$ group. Examples of such ethers are di-isopropyl-ether or methyl-t-butyl-ether. In another embodiment, the anti-solvent is an ester, preferably a $C_3$ to a $C_8$ ester, such as i-butyl-acetate.

The anti-solvent is preferably vigorously stirred, at a temperature of from about minus 20° C. to about positive 25° C., preferably from about minus 15° C. to about 0° C. Preferably, the solution is added slowly to the anti-solvent, such as dropwise. The term combining encompasses such dropwise addition. The resulting mixture can be stirred for about 4 to 24 hours. A precipitate forms which can be separated by techniques well known in the art. The precipitate can be dried in a fluidized bed dryer or in a vacuum oven at a temperature of about 35° C. As one of skill in the art can appreciate, other temperatures and conditions can also be used to dry the precipitate.

In an alternative embodiment, amorphous mupirocin calcium is prepared by a process comprising the steps of adding pseudomonic acid, a base and a source of calcium ions to a solvent selected from the group consisting of water, a $C_1$ to a $C_4$ alcohol and mixtures thereof to form a solution, and lyophilizing the solution. The amorphous form is lyophilized or freeze dried out of the solution, entirely skipping any crystallization or isolation step such as complete solvent removal or addition of an anti-solvent.

For lyophilization, in one embodiment, the solvent used is at least about 50% aqueous. The aqueous solvent is preferably water or a mixture of water and a $C_1$ to a $C_4$ alcohol. An exact amount for each component of the mixture is not required in the present invention. Rather, the mixture should have enough water to be aqueous in character. In one embodiment, the ratio of the water/solvent mixture is about 1:1 to 1:2 (vol/vol). In another embodiment, it is about 3:1 to 4:1 water/solvent. Higher water to solvent ratios are generally preferred. The alcohol is preferably a $C_1$ to a $C_4$ alcohol and most preferably methanol. Theoretically, amorphous mupirocin calcium can be lyophilized from just alcohol, but this process is avoided because of its health risks.

The solution may be modified to obtain a solution having water as a solvent, free of a co-solvent. This modification involves removal of solvents other than water, preferably by evaporation. Organic solvents such as alcohols, especially methanol, often have much higher volatility than water. This higher volatility makes it possible to selectively evaporate the organic solvent, under either ambient or reduced pressure. Preferably, the pressure is reduced.

The solution may optionally be heated to accelerate the process, though it is unnecessary when using high volatile solvents such as methanol. The temperature should not be raised beyond the melting point of the amorphous calcium mupirocin or induce any chemical reactions.

To substantially evaporate the alcohol, some water is probably also lost in the process. Even though water has a lower volatility, it nevertheless evaporates at a sufficient rate to cause loss of water. The lost water may be replaced, and optionally additional water may be added before freeze drying the solution to obtain the optimal volume for lyophilization.

The solution is lyophilized according to procedures well known in the art. Lyophilization is a stabilizing process in which a substance is first frozen and then the quantity of the solvent (generally water) is reduced, first by sublimation (referred to as the primary drying process) and then desorption (known as the secondary drying process) to values that will no longer support chemical reactions.

One of skill in the art would appreciate that many factors influence the efficiency of lyophilization and by changing these factors, the obtained sample may be modified. These factors include: surface area of sample, eutectic temperature, vacuum, condenser temperature, thickness of the sample, solute concentration and instrument factors.

Amorphous form produced by the above process, such as by solvent removal, lyophilization or by use of anti-solvent, can be used to obtain mupirocin calcium dihydrate. Since the amorphous form is already a calcium salt, a neutralization step and the addition of a calcium source is unnecessary. The process can simply be carried out in one step, by dissolving amorphous form to form an aqueous solution and crystallizing the dihydrate from the aqueous solution. For example, amorphous mupirocin calcium prepared by the above process can be dissolved in an ethanol/water mixture, followed by removal of the ethanol, and crystallization from water to recover the dihydrate.

More specifically, amorphous mupirocin calcium can be dissolved in water to prepare a solution. The temperature can be reduced to about 5° C. to accelerate crystallization. After about a few days, the crystals are separated. The dihydrate can be separated by techniques well known in the art, such as filtration. After separation, the dihydrate can be washed with water. Preferably, the dihydrate is subsequently dried. To dry, a temperature of about 25° C. to about 50° C. can be used for a sufficient amount of time.

In another embodiment for preparing the dihydrate from amorphous form, amorphous mupirocin calcium is dissolved in a water-miscible solvent. Preferably, a $C_1$ to a $C_4$ alcohol, such as methanol and ethanol is used. After preparing a solution in a lower alcohol, the solution is preferably diluted with water. The water content can be increased by removing the co-solvent, such as by evaporation. Preferably, the dihydrate is recovered by crystallizing out of a solution containing water free of a co-solvent.

In another aspect, the present invention provides a process for preparing mupirocin calcium dihydrate comprising the steps of adding pseudomonic acid and calcium oxide to water free of a co-solvent to form a solution, wherein mupirocin calcium dihydrate precipitates from the solution, separating the mupirocin calcium dihydrate and optionally converting the dihydrate to the anhydrate. Pseudomonic acid can be suspended in water. Calcium oxide can then be added to the suspension, followed by stirring and filtering. A co-solvent removal step is not necessary because a co-solvent is not used. The mixture can be cooled to about 5° C. and allowed to crystallize. The crystals can be separated by techniques well known in the art. An air circulating oven at room temperature can be used to dry the crystals.

In another aspect, the present invention provides a process for preparing crystalline mupirocin calcium dihydrate or an anhydrate thereof comprising the steps of preparing a solution of pseudomonic acid in a water-immiscible solvent, combining the solution with a solution or suspension of a calcium $C_2$ to $C_{12}$ organic carboxylate in an aqueous solvent, to form an aqueous and a non-aqueous phase, wherein mupirocin calcium dihydrate precipitates from the aqueous phase, separating the precipitate and optionally converting the dihydrate to the anhydrate.

Pseudomonic acid is first dissolved in a solvent that is immiscible in water. A water immiscible solvent refers to a solvent that can form a two phase system when combined with an aqueous solvent. One of skill in the art can appreciate that many such solvents exist, and that the preferred solvent can vary depending on the water content of the aqueous solvent. Preferred water immiscible solvents are those which pseudomonic acid can dissolve in to form a solution. Preferably, pseudomonic acid is dissolved in a ketone (preferably $C_3$ to $C_8$) such as t-butyl methyl ketone, an ether (preferably water immiscible ethers with each radical being $C_1$ to $C_4$) such as methyl t-butyl ether, or an ester (preferably water immiscible $C_3$-$C_8$ esters) such as ethyl acetate. The solvent can be heated to completely dissolve the pseudomonic acid. Preferably, the solvent is heated of about 40° C. to about 50° C.

After dissolution, an aqueous suspension or solution containing the calcium salt of an organic carboxylic acid, i.e., calcium carboxylate, is combined with the solution. The process results in an exchange of the acidic proton of pseudomonic acid for the calcium ion of the calcium carboxylate. In one embodiment, the solvent of the aqueous suspension or solution is water free of a co-solvent.

The term "organic carboxylic acid" is well-known in the art, and the term carboxylate refers to its charged ion where the acidic proton has been removed. Fatty acids are examples of organic carboxylic acids. The organic carboxylic acid used are branched and straight $C_2$ to $C_{12}$ carboxylic acids, with acetic, propionic and hexanoic acids being preferred, and hexanoic acid being more preferred. More preferably, the carboxylic acid is an alkylated hexanoic acid such as 2-ethyl-hexanoic acid.

The present invention encompasses embodiments where a calcium source and an organic carboxylate are added separately or when the ions of the organic calcium carboxylate have either partially or completely dissociated from each other before preparation of the final reaction mixture. The term calcium carboxylate encompasses these embodiment.

After combining the two liquids, a two phase system is created. Preferably, the two phase system is stirred for a few hours to about half a day, followed by separation of the two phases. The non-aqueous phase can be removed. The aqueous phase containing mupirocin calcium can be extracted with additional water-immiscible solvents to remove any excess organic carboxylic acid.

Mupirocin calcium dihydrate is then crystallized out of the aqueous phase. The aqueous phase can be diluted with water before crystallization for optimal crystallization. The resulting aqueous layer can be cooled to about 5° C. to accelerate crystallization. After crystallization, the dihydrate can be separated by techniques well-known in the art, such as filtration. After filtration, the dihydrate can optionally be washed. The dihydrate can optionally be dried under reduced pressure at slightly elevated temperatures of about 35° C. to remove residual solvents.

In another embodiment, the present invention provides a process for preparing crystalline mupirocin calcium dihydrate or an anhydrate thereof comprising the steps of adding pseudomonic acid and a calcium $C_2$ to $C_{12}$ organic carboxylate to an aqueous solvent to form a solution, wherein a $C_2$ to $C_{12}$ organic carboxylic acid forms, removing the carboxylic acid, separating mupirocin calcium dihydrate as a precipitate from the solvent and optionally converting the dihydrate to the anhydrate.

In one embodiment, pseudomonic acid is dissolved in an aqueous solvent, such as a methanol/water mixture, and is combined with another aqueous solution containing the calcium carboxylate. Most preferably, the carboxylate is calcium-2-ethyl-hexanoate. Other co-solvents, such as methanol, can be removed, preferably by evaporation, to obtain a solution having water as a solvent, free of a co-solvent. Most preferably, only a trace of other solvents remains.

After contact, 2-ethyl-hexanoic acid forms. A water-immiscible solvent, such as an ester (ethyl acetate), ether or ketone can be used to extract the acid, obtaining a two phase system. The aqueous phase is separated, preferably concentrated by evaporation and allowed to crystallize. After one or two days of crystallization at about room temperature, the crystals are separated, preferably by filtration. After separation, the crystals can optionally be washed with water. The crystals are preferably dried at a temperature of from about 25° C. to about 50° C., preferably no more than 45° C.

In another embodiment of the two phase system, the present invention provides a process for preparing crystalline mupirocin calcium hydrate or an anhydrate thereof comprising the steps of dissolving pseudomonic acid in a water-immiscible solvent to form a solution, combining the solution with a solution or suspension of a base and a source of calcium ions in an aqueous solvent, to form an aqueous and a non-aqueous phase, wherein the dihydrate precipitates from the aqueous phase, separating the dihydrate and optionally converting the dihydrate to the anhydrate. Suitable water immiscible solvents are those as described above. Preferably the solvent of the aqueous solution is water free of a co-solvent, to which a base and a source of calcium ions such as calcium oxide has been added. After mixing, a two phase system forms. The aqueous layer is separated. Mupirocin calcium dihydrate can then be crystallized out of the aqueous layer as described above, such as by cooling to about 5° C. and allowing for crystallization.

In another aspect, the present invention provides for desolvating the dihydrate to obtain crystalline anhydrous mupirocin calcium ("anhydrate form"). The term "dihydrate" refers to a solvate of water in which two water molecules ("water of crystallization") are part of the crystal structure in the solid phase. Baker et al. discloses that the dihydrate can be desolvated at a temperature of above about 70° C. Or the dihydrate can be dried in the presence of a drying agent such as phosphorus pentoxide, at a temperature range of from about 18° C. to 80° C. for a day. One of skill in the would appreciate that other conditions and techniques known in the art can also be used to desolvate the dihydrate.

The processes of the present invention can also be described in other terms, such as reacting pseudomonate ions with calcium ions in solution, and then lyophilizing, removing the solvent or using an anti-solvent to obtain amorphous form.

The PXRD data (FIGS. 1-5) disclosed further confirms the result of the processes. The PXRD data shows a pattern for the mupirocin calcium dihydrate.

The following table, Table 3, illustrates the purity data for the samples from the examples. The purity data in the table are area percentages and not assays.

TABLE 3

Purity of mupirocin calcium dihydrate

| Example # | Mupirocin Calcium Dihydrate Area % (Not Assay) |
|---|---|
| 9 | 98 |
| 10 | 98.2 |
| 11 | 97.5 |
| 13 | 97.8 |
| 16 | 97.6 |

Many processes of the present invention involve crystallization out of a particular solvent. One of skill in the art would appreciate that the conditions concerning crystallization may be modified without affecting the form of the polymorph obtained. For example, when mixing a solute in a solvent to form a solution, warming of the mixture may be necessary to completely dissolve the starting material. If warming does not clarify the mixture, the mixture may be diluted or filtered. To filter, the hot mixture may be passed through paper, glass fiber or other membrane material, or a clarifying agent such as celite. Depending upon the equipment used and the concentration and temperature of the solution, the filtration apparatus may need to be preheated to avoid premature crystallization.

The conditions may also be changed to induce or accelerate precipitation. A preferred way of inducing crystallization is to reduce the solubility of the solvent. The solubility of the solvent may be reduced, for example, by cooling the solvent.

Another manner to accelerate crystallization is by seeding with a crystal of the product or scratching the inner surface of the crystallization vessel with a glass rod. Other times, crystallization may occur spontaneously without any inducement. The present invention covers both embodiments where crystallization is induced/accelerated or occurs spontaneously. A separate crystallization step is not recited to emphasize that crystallization can occur spontaneously, but such emphasis is not meant to change the scope of the present invention from one reciting a crystallization step. One of skill in the art would appreciate that the conditions provided for crystallization in the present invention are for illustration, and that their modification may not necessarily change the result.

Pharmaceutical Compositions Containing Highly Purified Amorphous Calcium Mupirocin In accordance with the present invention, the highly pure calcium mupirocin, including the amorphous form, are prepared by the new methods disclosed herein. They may be prepared as pharmaceutical compositions that are particularly useful for the treatment of infections, particularly secondarily infected traumatic skin lesions. Such compositions comprise calcium mupirocin, such as the amorphous form, with pharmaceutically acceptable carriers and/or excipients known to one of skill in the art.

For example, these compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or anhydrous solution or emulsion, while for rectal administration suitable forms for administration include suppositories with hydrophilic or hydrophobic vehicle. For topical administration the invention provides suitable transdermal delivery systems known in the art or formulations that substantially remain local for topical use, and for nasal delivery there are provided suitable aerosol delivery systems known in the art.

The topical compositions of the present invention may be made as taught by the prior art. U.S. Pat. No. 4,879,287 is incorporated herein for the composition of a topical cream. The composition comprises preferably less than 50% active ingredient. More preferably less than 10% and most preferably about 2%. The composition may be administered with a corticosteroid content of less than about 5%, most preferably less than about 2%. U.S. Pat. No. 4,879,287 can be consulted for a full description of requirements for a topical cream. Bactroban® can also be used for guidance.

Pharmaceutical compositions of the present invention contain highly purified calcium mupirocin, including the amorphous form, optionally in mixture with other forms of mupirocin. In addition to the active ingredient(s), the pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of non-compacted solid composition and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the amorphous calcium mupirocin and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition according to the present invention may also contain a buffer such as guconic acid, lactic acid, citric acid or acetic acid, sodium guconate, sodium lactate, sodium citrate or sodium acetate.

Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The dosages may be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

An dosage form of the present invention is a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filing may be prepared by wet granulation. In wet granulation some or all of the active ingredients and excipients in powder form are blended and then further mixed in the presence of a liquid, typically water, that causes the powders to clump up into granules. The granulate is screened and/or milled, dried and then screened and/or milled to the desired particle size. The granulate may then be tableted or other excipients may be added prior to tableting such as a glidant and or lubricant.

A tableting composition may be prepared conventionally by dry blending. For instance, the blended composition of the actives and excipients may be compacted into a slug or a sheet and then comminuted into compacted granules. The compacted granules may be compressed subsequently into a tablet.

As an alternative to dry granulation, a blended composition may be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, only they are not subjected to a final tableting step.

A single oral dose of 500 mg base equivalent has been well tolerated and one of skill in the art may design capsules, tablets and lozenges and other unit dosage forms accordingly.

Characterization data was obtained in the following manner:

Thermal Stability
Glass ampoule in Aluminum laminate bag with silica gel was used as the packing system.
Relative humidity was exactly 60%.

Water Content
The water content was measured by the Karl Fischer method.

Powder X-Ray Diffraction
Instrument-Scintag X'TRA-030 X-ray diffractometer.
Software—DMSNT.
Radiation source was Copper (FK61-10CU).
X-ray Generator Model-20X2988, operated at 45 KV and 40 mA.
Detector-solid state.
Data was acquired with a scan rate of 3.00 Deg./min. at a range of 4-40.
Degree, step size 0.050°, Cnt time 1 sec.

DSC
Mettler TA 3000, DSC 20
heating interval—25-250° C.
heating rate—5° C./min.
atmosphere—Nitrogen, 40 m/min.
sample holder—Al crucible with holes TG
Mettler TA 3000, TG 50
heating interval—25-250° C.
heating rate—5° C./min.
atmosphere—Nitrogen, 40 ml/min.
sample holder—Ceramic 150 ml IR
Perkin Elmer FTIR SPECTRUM 1000
Spectra was taken in KBr pellet in the range of 4000-400 $cm^{-1}$ Determination of Impurities for Mupirocin-Calcium
High pressure liquid chromatography (HPLC) was performed on a Zorbax® C-8 (5 um; 250×4.6 mm), reverse phase column with ammonium acetate buffer solution in water: tetrahydrofuran mixture as eluent. Detected by U.V. spectroscopy at $\lambda$=240 nm.

Determination of Impurities for Pseudomonic Acid
High pressure liquid chromatography (HPLC) was performed on a Hypersil Shandan BDS® C-18 (3 um; 100×4.6 mm), reverse phase column with sodium-dihydrogen-phosphate buffer solution in water: acetonitrile mixture as gradient eluent. Detected by U.V. spectroscopy at $\lambda$=229 nm.

The assay also used the same HPLC instruments.

EXAMPLES

Example 1

Preparation of Mupirocin Calcium Dihydrate

Amorphous mupirocin calcium (2.50 g, 2.40 mmole) was dissolved in water (10 ml) and stirred to give a clear solution. The mupirocin calcium solution was allowed to crystallize for 60 h at 5° C. The crystalline product was filtered and washed with water (5 ml). The crystalline product was dried at 45° C. for 6 h.

Example 2

Preparation of Mupirocin Calcium Dihydrate

Amorphous mupirocin calcium (5.00 g, 4.80 mmole) was dissolved in methanol (15 ml) and stirred to give a clear solution. Water (10 ml) was added to the solution. Methanol from the solution was evaporated at reduced pressure to give a final volume of 7 ml. The mupirocin calcium solution was allowed to crystallize for 60 h at 5° C. The crystalline product was filtered and washed with water (5 ml). The product was dried at 30° C. for 12 h.

Example 3

Preparation of Mupirocin Calcium Dihydrate

Pseudomonic acid (2.50 g, 10 mmole) was dissolved in a mixture of methanol and water (30 ml and 30 ml). Calcium 2-ethyl-hexanoate (0.92 g, 5.00 mmole) was dissolved in a mixture of methanol and water (60 ml and 30 ml). The calcium 2-ethyl-hexanoate solution was added to the pseudomonic acid solution, and stirred for 1 h. The methanol was evaporated from the solution at reduced pressure to give a final volume of 60 ml. The 2-ethyl hexanoic acid was extracted with ethyl-acetate (2×40 ml), and the aqueous layer was evaporated from the solution at reduced pressure to give a final volume of 50 ml. The mupirocin calcium solution was allowed to crystallize for 36 h at room temperature. The crystalline product was filtered and washed with water (10 $cm^3$). The product was dried at 40° C. for 8 h.

Example 4

Preparation of Amorphous Mupirocin Calcium

Pseudomonic acid (4000 g, 8 mole) was dissolved in ethanol (10 l). Ethanolic solution of potassium hydroxide (448.88 g, 8 mole potassium hydroxide and 2.6:1 ethanol) and ethanolic solution of calcium chloride (443.96 g, 5.0 mmole calcium chloride and 2.6:1 ethanol) was added to the mixture. The mixture was stirred for 90 minutes and then filtered to remove potassium chloride. Then, 3:1 ethanol was added to the solution and the ethanol was evaporated at reduced pressure to give a final volume of 10:1 (Solution A). Ethanol was evaporated from 1400 ml of Solution A with rotary evaporation at reduced pressure to give a solid, white foam. The product was dried for 12 h at 45° C. under vacuum.

Example 5

Preparation of Mupirocin Calcium Dihydrate

Water (20 ml) was added to a mupirocin calcium ethanolic concentrate (50.84 g, ca. 37 m/m %) prepared generally by the same technique as the prior example. The ethanol from the solution was evaporated at reduced pressure to give a final volume of 20 ml. The mupirocin calcium solution was allowed to crystallize for 24 h at 5° C. The crystalline product was filtered and washed with water (15 ml). The product was dried at 30° C. for 12 h.

The water from the filtrate was evaporated at reduced pressure to give a final volume of 5 ml. The mupirocin calcium solution was allowed to crystallize for 24 h at 5° C. The crystalline product was filtered and washed with water (2×15 ml). The product was dried at 30° C. for 12 h.

Example 6

Preparation of Mupirocin Calcium Dihydrate

Pseudomonic acid (10 g) was suspended in water (26 ml). Calcium oxide (0.58 g) was added to the suspension. The mixture was stirred for one hour, and filtered. The mixture was cooled to 5° C. After standing for 15 h, the crystalline product was filtered and washed with cooled water (10 ml) and dried in an air circulated oven at room temperature. Mupirocin calcium dihydrate (9.4 g, 87%) was obtained.

Figure 1:
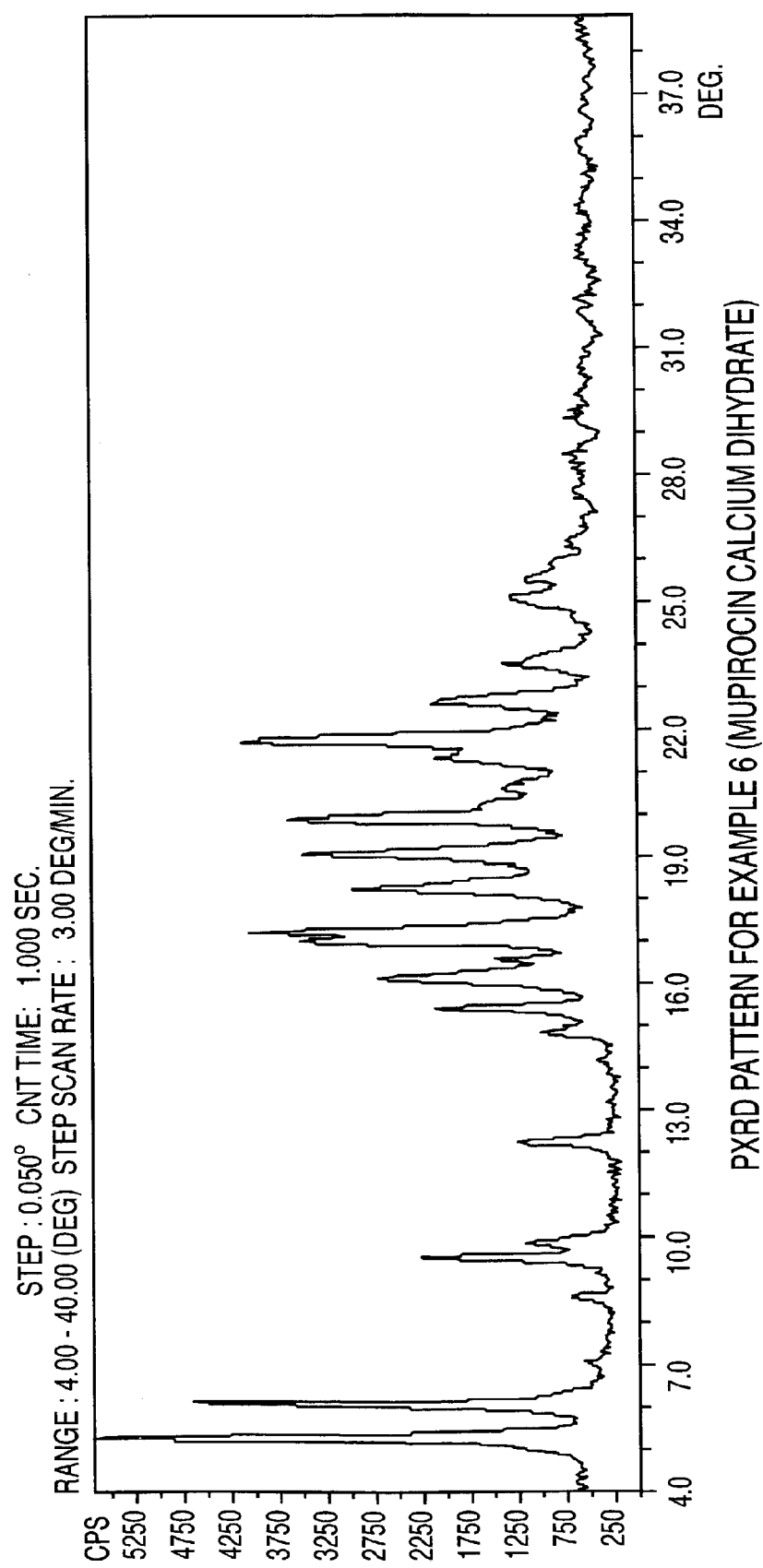
FIG. 1 is a Powder X-ray Diffraction ("PXRD") pattern of the product of Example 6.

PXRD confirmation data attached (FIG. 1).

Example 7

Preparation of Mupirocin Calcium Dihydrate

Amorphous mupirocin calcium (14 g) was dissolved in water (35 ml) and stirred for one hour. The mixture was cooled to 5° C. and kept at this temperature for 15 hours. Then mixture was then stirred at 5° C. for 3 hours. The crystalline product was filtered and dried in an air circulated oven at room temperature. Mupirocin calcium dihydrate (12.5 g, 83%) was obtained.

Example 8

Preparation of Mupirocin Calcium Dihydrate

Amorphous mupirocin calcium (20.00 g, 19.20 mmole) was added into water (20 ml) under stirring. The slurry was stirred for 0.5 hour, and then it was cooled to 5° C. The mupirocin calcium solution was allowed to crystallize for 16 h. The crystal slurry was diluted with 15 ml water, and the crystals were filtered and washed with water (5 ml). The product (17.1 g) was dried at 35° C. for 12 h.

Example 9

Preparation of Mupirocin Calcium Dihydrate

Pseudomonic acid (10 g) was dissolved in isobutyl methyl ketone (120 ml). Calcium oxide (0.57 g) was suspended in water (68 ml), and added to the solution of pseudomonic acid. The mixture was stirred for one hour, and the phases were separated. The volume of the aqueous phase was reduced to 40 ml by vacuum distillation. The mixture was cooled to 5° C., and after standing for 15 hours, the crystalline product was filtered and washed with cooled water (10 ml). The product was then dried in an air circulated oven at RT. Mupirocin calcium dihydrate (3.7 g, 35%) was obtained.

Figure 2:
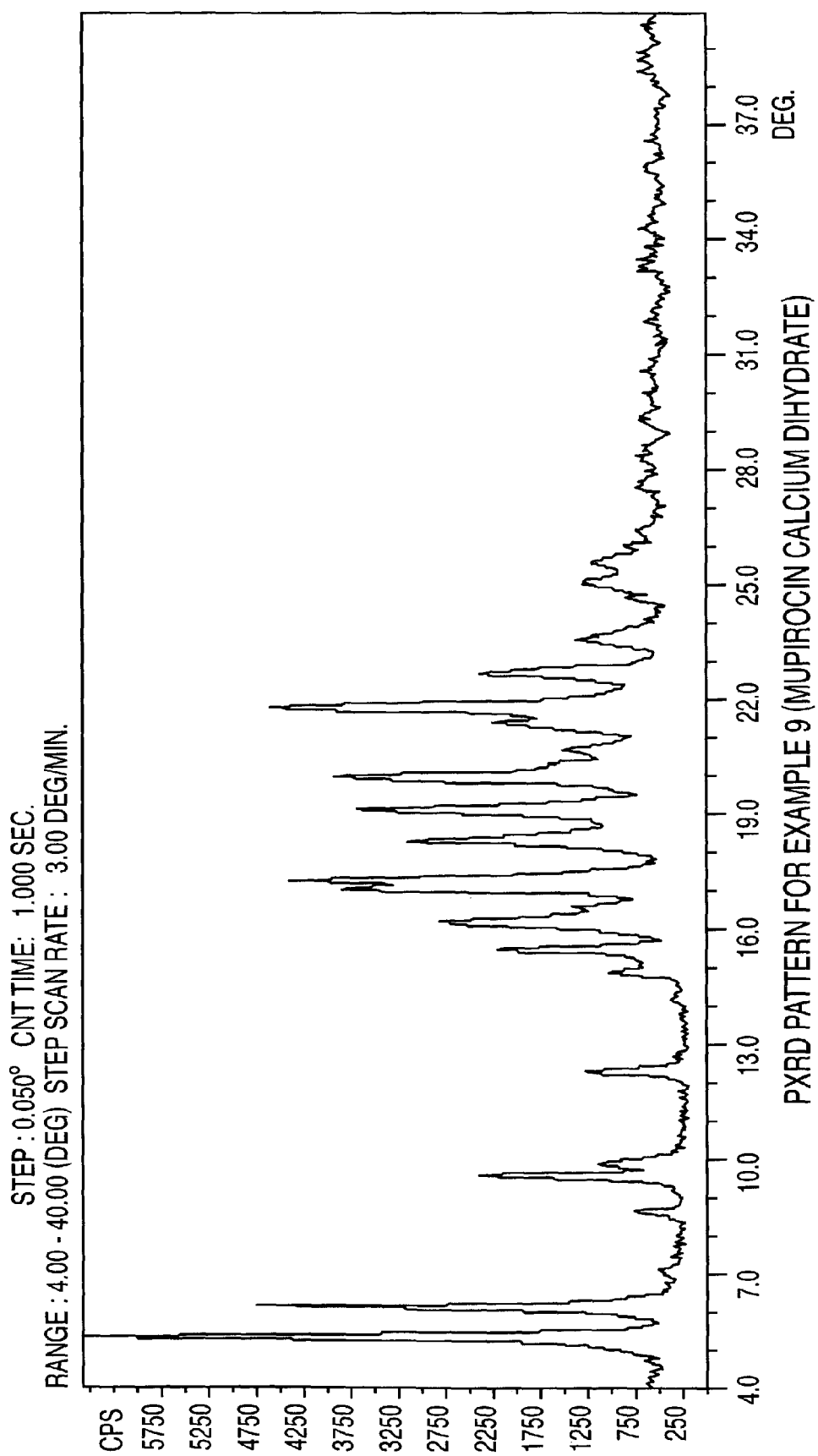
FIG. 2 is a PXRD pattern of the product of Example 9.

PXRD confirmation data is attached (FIG. 2).

Example 10

Preparation of Mupirocin Calcium Dihydrate

Pseudomonic acid (10.00 g, 20 mmole) was dissolved in 100 ml of ethyl acetate at 40° C. Calcium-2-ethyl-hexanoate (3.32 g, 10 mmole) was suspended in 25 ml of water. The solution of pseudomonic acid was added to the calcium-2-ethyl-hexanoate suspension, and the resulting two phases system were stirred for 14 hours. The two phases were then separated, and any traces of ethyl acetate was evaporated from the aqueous phase. The aqueous mupirocin calcium suspension was cooled in the refrigerator to 5° C. and precipitated. The solid mupirocin calcium dihydrate was subsequently filtered, washed with 10 ml water and dried under vacuum at 35° C. for 14 hours. The mass of the product was 7.82 grams.

Figure 3:
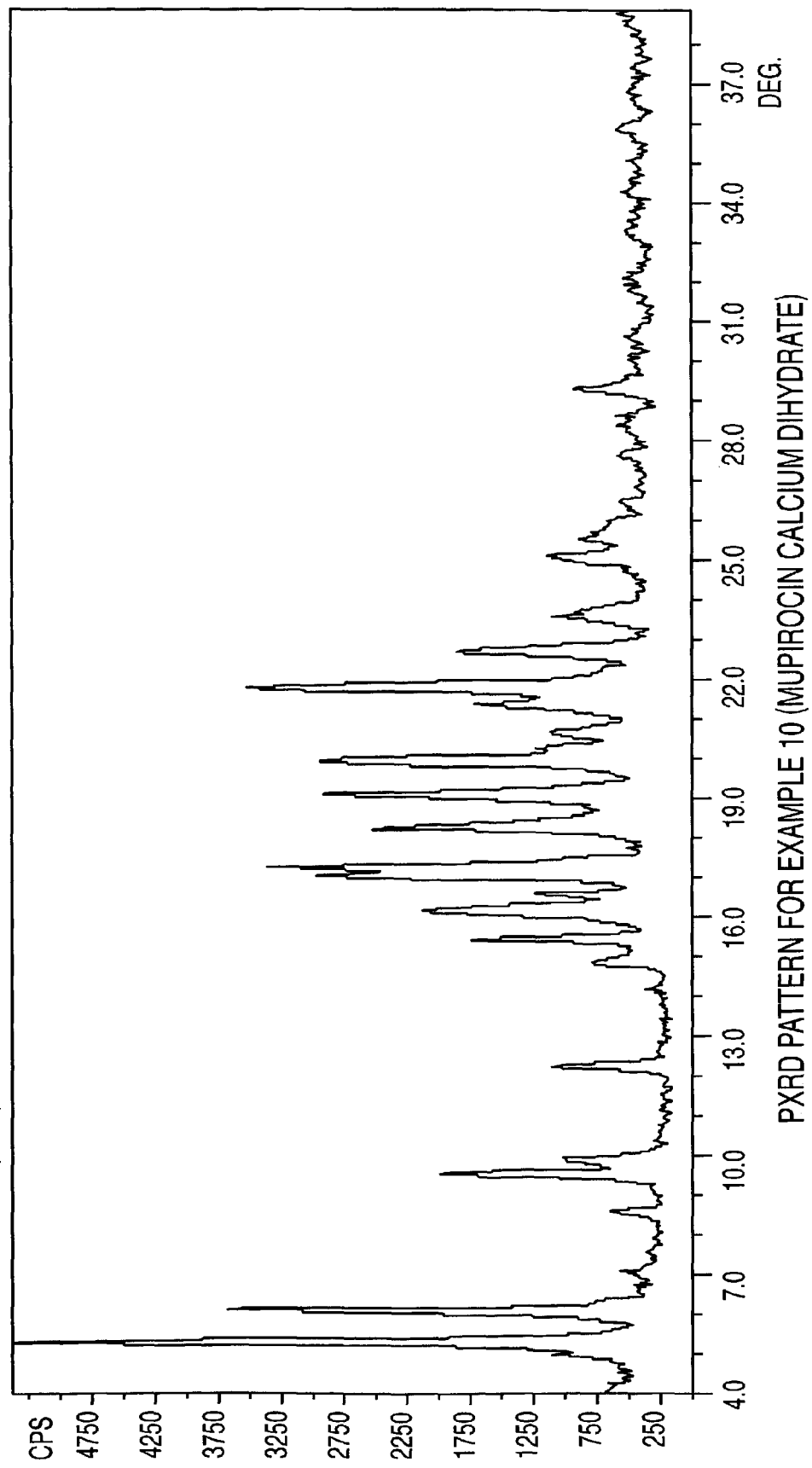
FIG. 3 is a PXRD pattern of the product of Example 10.

PXRD confirmation data is attached. (FIG. 3).

Example 11

Preparation of Mupirocin Calcium Dihydrate

Pseudomonic acid (10.00 g, 20 mmole) was dissolved in methyl tertbutyl ether (150 ml) at 45° C. Calcium-2-ethyl-hexanoate (3.32 g, 10 mmole) was suspended in water (30 ml). The solution of pseudomonic acid was added to the calcium-2-ethyl-hexanoate suspension, and the resulting two phases system were stirred for 14 hours. The two phases were then separated, and water (20 ml) and methyl tertbutyl ether (50 ml) was added to the aqueous phase, and was stirred for 10 minutes. The resulting two phases were separated, and any traces of methyl tertbutyl ether was evaporated from the aqueous phase. The aqueous mupirocin calcium suspension was cooled in a refrigerator at 5° C. The solid mupirocin calcium dihydrate was filtered, washed with 20 ml water and dried under vacuum at 35° C. for 5 hours. The mass of product was 5.88 grams.

Example 12

Preparation of Mupirocin Calcium Dihydrate

Pseudomonic acid (10.00 g, 20 mmole) was dissolved in methyl tertbutyl ether (180 ml) at 40° C. Calcium-2-ethyl-hexanoate (3.32 g, 10 mmole) was suspended in water (50 ml). (It is possible to obtain a solution by using a larger amount of water or an alcohol/water mixture). The solution of pseudomonic acid was added to the calcium-2-ethyl-hexanoate suspension, and the two phase system was stirred for 24 hours. The two phases were separated, 50 ml methyl tertbutyl ether was added to the aqueous phase and stirred for 10 minutes. The two resulting phases were separated, and the methyl tertbutyl ether was evaporated from the aqueous phase. The aqueous mupirocin calcium suspension was cooled in the refrigerator at 5° C. The solid mupirocin calcium dihydrate was filtered, washed with water (20 ml) and dried under vacuum at 35° C. for 14 hours. The mass of product was 8.65 grams. Assay: 95.68%, water: 3.48%

Example 13

Preparation of Mupirocin Calcium Dihydrate

Pseudomonic acid (10.00 g, 20 mmole) was dissolved in isobutyl methyl ketone (100 ml) at 40° C. Calcium-2-ethyl-hexanoate (3.32 g, 10 mmole) was suspended in water (50 ml). (It is possible to obtain a solution by using a larger amount of water or an alcohol/water mixture). The solution of pseudomonic acid was added to the calcium-2-ethyl-hexanoate suspension, and the two phase system were stirred for 24 hours. The two phases were then separated, isobutyl methyl ketone (25 ml) was added to the aqueous phase, and stirred for 10 minutes. The two resulting phases were separated, and any traces of isobutyl methyl ketone was evaporated from the aqueous phase. The aqueous mupirocin calcium suspension was cooled in a refrigerator at 5° C. The solid mupirocin calcium dihydrate was filtered, washed with water (20 ml) and dried under vacuum at 35° C. for 14 hours. The mass of product was 7.95 grams. Assay 97.72%, water: 3.45%.

Example 14

Preparation of Mupirocin Calcium Dihydrate

Pseudomonic acid (10.00 g, 20 mmole) was dissolved in a mixture of methanol (30 ml) and water (15 ml). Calcium 2-ethyl-hexanoate (3.32 g, 10.00 mmole) was dissolved in a mixture of methanol (60 ml) and water (30 ml). The calcium 2-ethyl-hexanoate solution added to the pseudomonic acid solution and was stirred for 1 h. The methanol was evaporated from the solution at reduced pressure to give a final volume of 45 ml. Water (15 ml) was added from the solution. The 2-ethyl hexanoic acid was extracted with ethyl-acetate (3×20 ml) and the aqueous layer was evaporated from the solution at reduced pressure to give a final volume of 60 ml. The mupirocin calcium solution was allowed to crystallize for 36 h at 5° C. temperature. The crystalline product was filtered and washed with water (10 ml). The product (3.6 g) was dried at 35° C. for 8 h.
Assay: 96.9%
Water: 3.0%
(This assay is expressed differently than those for amorphous form. Table-1 should be consulted in regard to this matter).

Example 15

Preparation of Mupirocin Calcium Dihydrate

Figure 4:
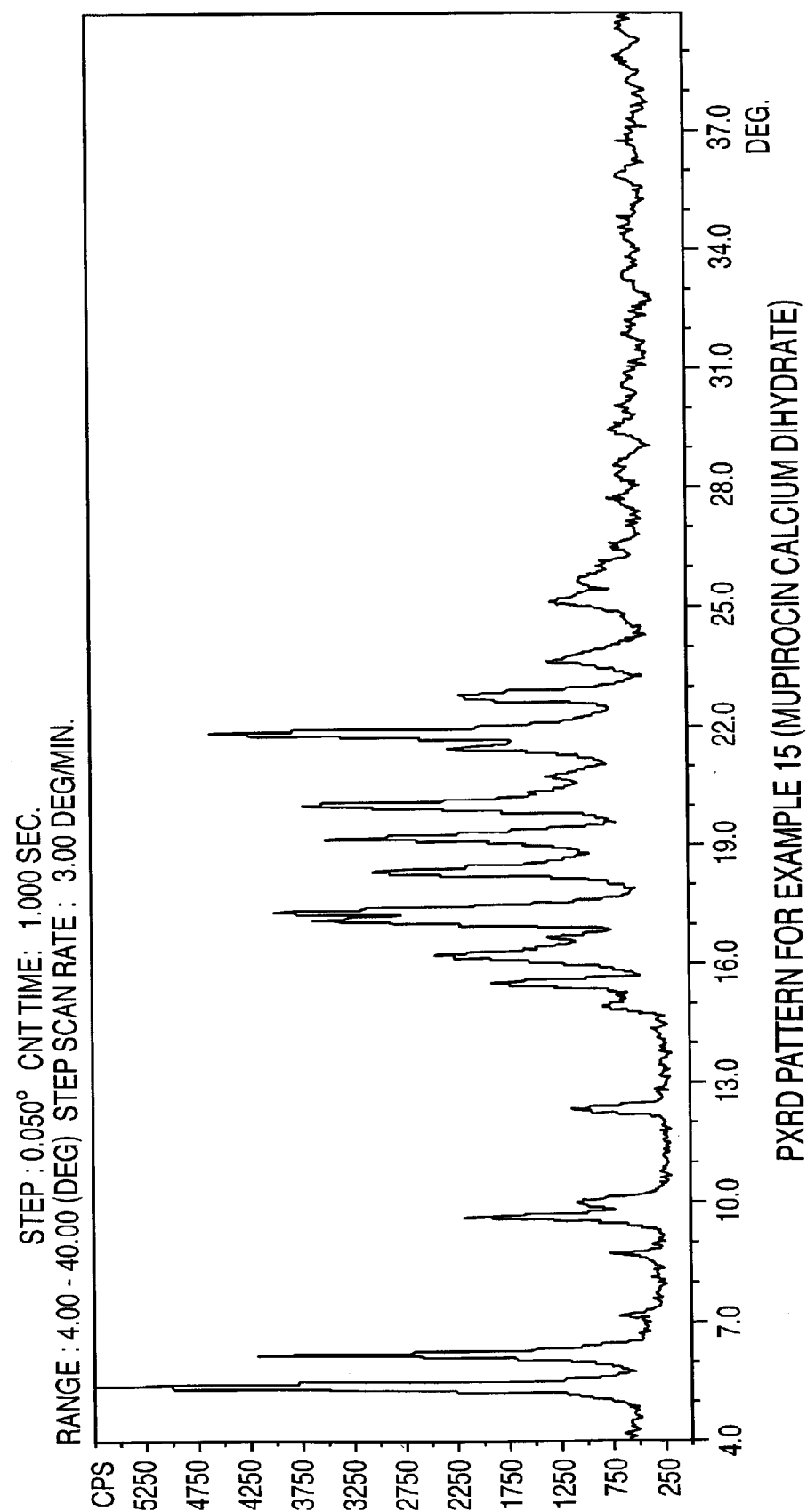
FIG. 4 is a PXRD pattern of the product of Example 15.
Figure 5:
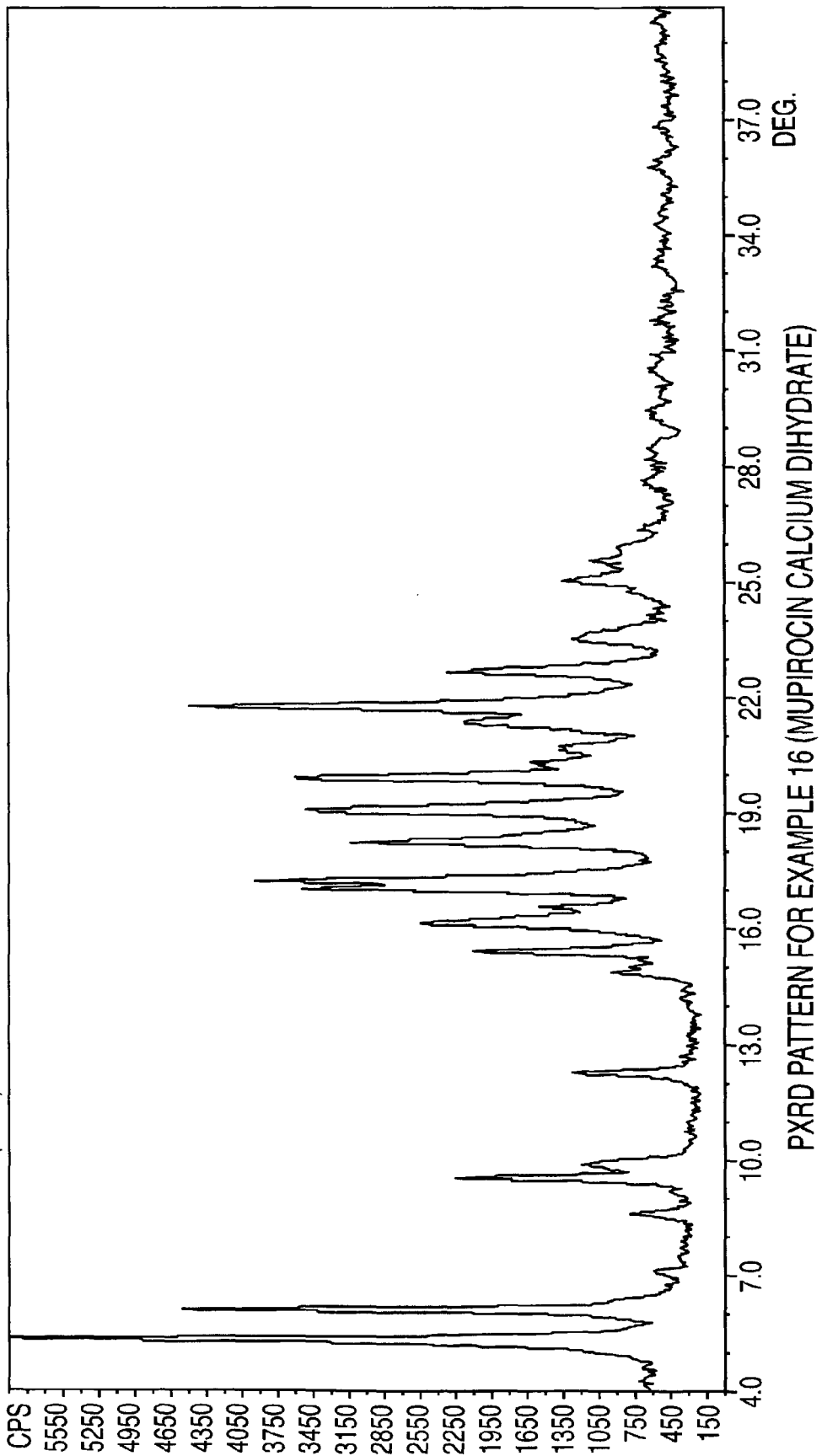
FIG. 5 is a PXRD pattern of the product of Example 16.

Pseudomonic acid (50.00 g, 0.10 mole) was dissolved in methanol (150 ml). Calcium 2-ethyl-hexanoate (15.92 g, 48.00 mmole) was suspended in a mixture of methanol/water (250 ml and 125 ml). The pseudomonic acid solution added to the calcium 2-ethyl-hexanoate solution and was stirred for 1 h. The methanol was evaporated from the solution at reduced pressure to give a final volume of 125 ml. The 2-ethyl hexanoic acid was extracted with ethyl-acetate (4×50 ml), and the aqueous layer was evaporated from the solution at reduced pressure to give a final volume of 125 ml. The mupirocin calcium solution was allowed to crystallize for 48 h at 5° C. temperature. The crystalline product was filtered and washed with water (10 ml). The product (18.4 g) was dried at 35° C. for 8 h.
PXRD confirmation data is attached. (FIG. 4)

Example 16

Preparation of Mupirocin Calcium Dihydrate

Pseudomonic acid was dissolved in isobutyl acetate (130 ml). Calcium oxide (0.29 g) was suspended in water (32 ml) and added to the solution of pseudomonic acid. The mixture was stirred for 2 hours, and the phases were separated. The volume of the aqueous phase was reduced to 15 ml by vacuum distillation. The mixture was cooled to 5° C. After stirring for 2 hours, the crystalline product was filtered and washed with cooled water (5 ml). The product was dried in an air circulated oven at RT. Mupirocin calcium dihydrate (3.3 g, 62%) was obtained.

Example 17

Preparation of Amorphous Mupirocin Calcium

Pseudomonic acid (5.00 g, 10 mmole) was dissolved in methanol (5.5 ml), methanolic solution of potassium hydroxide (0.56 g, 10 mmole potassium hydroxide and 4 ml methanol) and methanolic solution of calcium chloride (0.56 g, 5.0 mmole calcium chloride and 5 ml methanol) were added to the mixture. The mixture was stirred for 1 hour. The solution was then filtered to remove potassium chloride (0.60 g). The methanol was then evaporated at reduced pressure to give a solid, white foam. The product was dried for 12 hours at 45° C. under vacuum to obtain 4.85 grams of final product. Assay: 95.9%, Water: 2.23% [total impurity: 3.19%, highest impurity: 1.23%-different method than assay], melting point: 85 to 89° C.

Example 18

Preparation of Amorphous Mupirocin Calcium

Pseudomonic acid (5.00 g, 10 mmole) was dissolved in ethanol (20 ml), ethanolic solution of potassium hydroxide (0.56 g, 10 mmole potassium hydroxide and 10 ml ethanol) and ethanolic solution of calcium chloride (0.56 g, 5.0 mmole calcium chloride and 10 ml ethanol) were added to the mixture. The mixture was stirred for 1 hour and the solution was filtered to remove potassium chloride (0.51 g). The ethanol was subsequently evaporated at reduced pressure to give a solid, white foam. The product was dried for 12 hours at 45° C. under vacuum. The product had a mass of 4.38 grams. Assay: 99.1%, water: 2.36% [total impurity: 2.44%, highest impurity: 1.10% different method than the assay].

Example 19

Preparation of Amorphous Mupirocin Calcium

Pseudomonic acid (4000 g, 8 mole) was dissolved in ethanol (10 l), ethanolic solution of potassium hydroxide (448.88 g, 8 mole potassium hydroxide and 2.6:1 ethanol) and ethanolic solution of calcium chloride (443.96 g, 5.0 mmole calcium chloride and 2.6:1 ethanol) were added to the mixture. The mixture was stirred for 90 minutes, and the solution was filtered to remove potassium chloride. Ethanol was added to the solution in a 1:3 ratio, and the ethanol was evaporated at reduced pressure to give a final volume of 10:1 (Solution A).

Ethanol was evaporated from Solution A (350 ml) with a rotary evaporation at reduced pressure to give a solid, white foam. The product was dried for 12 hours at 45° C. under vacuum to give a final product with a mass of 110.02 grams.
Assay: 98.2%, water 0.36%, melting point: 84-86° C.

Ethanol was evaporated from 1400 ml of Solution A with a rotary evaporation at reduced pressure to give a solid, white foam. The product was dried for 12 h at 45° C. under vacuum to give a mass of 513.18 grams.

Assay: 96.8% [total impurity: 3.66%, highest impurity: 1.29%-different method than the assay], melting point: 85-86° C.

Example 20

Preparation of Amorphous Mupirocin Calcium

Pseudomonic acid (220 g) was dissolved in methanol (210 ml) kept at 25-27° C. Separately, potassium hydroxide (27.9 g) was dissolved in methanol (154 ml). Also separately, calcium chloride (24.39 g) was dissolved in methanol (133 ml). The potassium hydroxide solution was added to the pseudomonic acid solution until obtaining a pH=9.4-9.5 (147 ml of potassium hydroxide solution was added.). The calcium chloride solution was then added to the mupirocin potassium solution until reaching a pH=7.6-7.7 (128 ml of calcium chloride solution was added.). The solution was stirred at 24-25° C. for an hour. Potassium chloride was filtered, and the solution was labeled Solution B. Solution B (25 ml) was added to diisopropyl-ether (250 ml) at (−7)° C. while stirring. Solid amorphous mupirocin calcium precipitated from the solution, and was stirred at −7° C. for 3 h. The solid product was filtered and washed with cold diisoprpyl-ether (10 ml). The product was dried in a fluidized bed dryer for 6 hours at 35° C., and then in a vacuum oven for 12 h at 35° C.

Example 21

Preparation of Amorphous Mupirocin Calcium by Lyophilization

Pseudomonic acid (10.01 g, 20 mmole) was dissolved in a mixture of methanol/water (50 ml and 36 ml). Calcium oxide (0.78 g, 14 mmole) was added portionwise to the mixture and was stirred for 1 h. The solution was filtered, and the methanol was evaporated from the filtrate at reduced pressure to give a final volume of 30 ml. Water (20 ml) was added to the solution. Then the solution was freeze dried to obtain 9.11 grams of product.

Assay: 100%, water: 1.59%, melting point: 84-86° C., [total impurity: 2.64%, highest impurity: 1.35%—different method than the assay], melting point: 84-86° C.

Having thus described the invention with reference to particular preferred embodiments and illustrated it with examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of conventional methods relating to solid state chemistry are discussed in Polymorphism in *Pharmaceutical Solids, Drugs and the Pharmaceutical Sciences*, vol. 95. All references mentioned herein are incorporated in their entirety.

What is claimed is:

1. A pharmaceutical composition comprising:
   a) amorphous mupirocin calcium characterized by a melting point of 85° C. to about 89° C.; and
   b) a pharmaceutically acceptable excipient.

2. A method of treating bacterial infections of the skin susceptible to mupirocin calcium comprising administering the pharmaceutical composition of claim 1 to an animal.

3. Amorphous mupirocin calcium characterized by a melting point of 85° C. to about 89° C.

4. A pharmaceutical composition prepared by a process comprising:
   a) providing amorphous mupirocin calcium characterized by a melting point of 85° C. to about 89° C.; and
   b) combining the amorphous form with a pharmaceutically acceptable excipient to obtain the pharmaceutical composition.

* * * * *